United States Patent
Stuart et al.

(10) Patent No.: US 12,093,036 B2
(45) Date of Patent: Sep. 17, 2024

(54) TELEROBOTIC SYSTEM WITH A DUAL APPLICATION SCREEN PRESENTATION

(75) Inventors: David A. Stuart, Santa Barbara, CA (US); Michael C. Chan, Santa Barbara, CA (US); Timothy Wright, Santa Barbara, CA (US); Yulun Wang, Goleta, CA (US); Fuji Lai, Goleta, CA (US)

(73) Assignee: TELADOC HEALTH, INC., Purchase, NY (US)

(*) Notice: Subject to any disclaimer, the term of this patent is extended or adjusted under 35 U.S.C. 154(b) by 90 days.

(21) Appl. No.: 13/011,018

(22) Filed: Jan. 21, 2011

(65) Prior Publication Data

US 2012/0191464 A1    Jul. 26, 2012

(51) Int. Cl.
*G16H 30/20* (2018.01)
*G05D 1/00* (2006.01)
*G16H 40/67* (2018.01)
*H04N 7/18* (2006.01)

(52) U.S. Cl.
CPC .......... *G05D 1/0038* (2013.01); *G16H 30/20* (2018.01); *G16H 40/67* (2018.01); *H04N 7/183* (2013.01)

(58) Field of Classification Search
CPC ......... G05D 1/0038; G05D 2201/0206; H04N 7/183; G06Q 50/22; G06F 19/3418
See application file for complete search history.

(56) References Cited

U.S. PATENT DOCUMENTS

| | | | |
|---|---|---|---|
| 3,821,995 | A | 7/1974 | Aghnides |
| 4,107,689 | A | 8/1978 | Jellinek |
| 4,213,182 | A | 7/1980 | Eichelberger et al. |
| 4,413,693 | A | 11/1983 | Derby |
| 4,471,354 | A | 8/1984 | Smith |
| 4,519,466 | A | 5/1985 | Shiraishi |
| 4,553,309 | A | 11/1985 | Hess et al. |

(Continued)

FOREIGN PATENT DOCUMENTS

| | | |
|---|---|---|
| AU | 1216200 A | 5/2000 |
| CA | 2289697 | 11/1998 |

(Continued)

OTHER PUBLICATIONS

Adams, Chris, "Mobile Robotics Research Group", Mobile Robotics Research Group, Edinburgh University, http://www.dai.ed.ac.uk/groups/mrg/MRG.html, Internet, Edinburgh. duplicate of 575084, 2000, pp. 1-2.

(Continued)

*Primary Examiner* — Chad A Newton

(57) ABSTRACT

A proctoring system that includes a communication device coupled to a remote station. The remote station has a visual display that displays first information relating to an action that causes an effect on an object, and simultaneously displays second information relating to the effect on the object. The remote station includes at least one input device that allows a communication to be transmitted by an operator to the communication device. By way of example, during the deployment of a heart stent, a specialist doctor may remotely view real-time fluoroscopy imagery and patient hemodynamics. The specialist can remotely proctor medical personnel on the proper orientation and timing requirements for installing the stent.

6 Claims, 3 Drawing Sheets

(56) References Cited

U.S. PATENT DOCUMENTS

| | | |
|---|---|---|
| 4,572,594 A | 2/1986 | Schwartz |
| 4,625,274 A | 11/1986 | Schroeder |
| 4,638,445 A | 1/1987 | Mattaboni |
| 4,652,204 A | 3/1987 | Arnett |
| 4,669,168 A | 6/1987 | Tamura et al. |
| 4,679,152 A | 7/1987 | Perdue |
| 4,697,278 A | 9/1987 | Fleischer |
| 4,697,472 A | 10/1987 | Hiyane |
| 4,709,265 A | 11/1987 | Silverman et al. |
| 4,733,737 A | 3/1988 | Falamak |
| 4,751,658 A | 6/1988 | Kadonoff et al. |
| 4,766,581 A | 8/1988 | Korn et al. |
| 4,777,416 A | 11/1988 | George et al. |
| 4,797,557 A | 1/1989 | Ohman |
| 4,803,625 A | 2/1989 | Fu et al. |
| 4,847,764 A | 7/1989 | Halvorson |
| 4,875,172 A | 10/1989 | Kanayama |
| 4,878,501 A | 11/1989 | Shue |
| 4,942,512 A | 7/1990 | Kohno |
| 4,942,538 A | 7/1990 | Yuan et al. |
| 4,953,159 A | 8/1990 | Hayden et al. |
| 4,974,607 A | 12/1990 | Miwa |
| 4,977,971 A | 12/1990 | Crane et al. |
| 5,006,988 A | 4/1991 | Borenstein et al. |
| 5,040,116 A | 8/1991 | Evans, Jr. et al. |
| 5,051,906 A | 9/1991 | Evans, Jr. et al. |
| 5,073,749 A | 12/1991 | Kanayama |
| 5,084,828 A | 1/1992 | Kaufman |
| 5,130,794 A | 7/1992 | Ritchey |
| 5,148,591 A | 9/1992 | Pryor |
| 5,153,833 A | 10/1992 | Gordon et al. |
| 5,155,684 A | 10/1992 | Burke et al. |
| 5,157,491 A | 10/1992 | Kassatly |
| 5,182,641 A | 1/1993 | Diner et al. |
| 5,186,270 A | 2/1993 | West |
| 5,193,143 A | 3/1993 | Kaemmerer et al. |
| 5,217,453 A | 6/1993 | Wilk |
| 5,220,263 A | 6/1993 | Onishi et al. |
| 5,224,157 A | 6/1993 | Yamada et al. |
| 5,230,023 A | 7/1993 | Nakano |
| 5,231,693 A | 7/1993 | Backes et al. |
| 5,236,432 A | 8/1993 | Matsen, III et al. |
| 5,262,944 A | 11/1993 | Weisner et al. |
| 5,305,427 A | 4/1994 | Nagata |
| 5,315,287 A | 5/1994 | Sol |
| 5,319,611 A | 6/1994 | Korba |
| 5,341,242 A | 8/1994 | Gilboa et al. |
| 5,341,459 A | 8/1994 | Backes |
| 5,341,854 A | 8/1994 | Zezulka et al. |
| 5,347,306 A | 9/1994 | Nitta |
| 5,347,457 A | 9/1994 | Tanaka et al. |
| 5,350,033 A | 9/1994 | Kraft |
| 5,366,896 A | 11/1994 | Margrey |
| 5,374,879 A | 12/1994 | Pin |
| 5,375,195 A | 12/1994 | Johnston |
| 5,400,068 A | 3/1995 | Ishida et al. |
| 5,413,693 A | 5/1995 | Redepenning |
| 5,417,210 A | 5/1995 | Funda et al. |
| 5,419,008 A | 5/1995 | West |
| 5,436,542 A | 7/1995 | Petelin et al. |
| 5,441,042 A | 8/1995 | Putman |
| 5,441,047 A | 8/1995 | David |
| 5,442,728 A | 8/1995 | Kaufman et al. |
| 5,462,051 A | 10/1995 | Oka |
| 5,486,853 A | 1/1996 | Baxter et al. |
| 5,510,832 A | 4/1996 | Garcia |
| 5,511,147 A | 4/1996 | Abdel-Malek |
| 5,528,289 A | 6/1996 | Cortjens et al. |
| 5,539,741 A | 7/1996 | Barraclough et al. |
| 5,544,649 A | 8/1996 | David et al. |
| 5,550,577 A | 8/1996 | Verbiest et al. |
| 5,553,609 A | 9/1996 | Chen et al. |
| 5,563,998 A | 10/1996 | Yaksich et al. |
| 5,572,229 A | 11/1996 | Fisher |
| 5,572,999 A | 11/1996 | Funda et al. |
| 5,594,859 A | 1/1997 | Palmer et al. |
| 5,600,573 A | 2/1997 | Hendricks et al. |
| 5,617,539 A | 4/1997 | Ludwig et al. |
| 5,619,341 A | 4/1997 | Auyeung et al. |
| 5,623,679 A | 4/1997 | Rivette et al. |
| 5,630,566 A | 5/1997 | Case |
| 5,636,218 A | 6/1997 | Ishikawa et al. |
| 5,652,849 A | 7/1997 | Conway et al. |
| 5,657,246 A | 8/1997 | Hogan et al. |
| 5,659,779 A | 8/1997 | Laird et al. |
| 5,673,082 A | 9/1997 | Wells et al. |
| 5,675,229 A | 10/1997 | Thorne |
| 5,682,199 A | 10/1997 | Lankford |
| 5,684,695 A | 11/1997 | Bauer |
| 5,701,904 A | 12/1997 | Simmons et al. |
| 5,734,805 A | 3/1998 | Isensee et al. |
| 5,739,657 A | 4/1998 | Takayama et al. |
| 5,748,629 A | 5/1998 | Caldara et al. |
| 5,749,058 A | 5/1998 | Hashimoto |
| 5,749,362 A | 5/1998 | Funda et al. |
| 5,754,631 A | 5/1998 | Cave |
| 5,758,079 A | 5/1998 | Ludwig et al. |
| 5,762,458 A | 6/1998 | Wang et al. |
| 5,764,731 A | 6/1998 | Yablon |
| 5,767,897 A | 6/1998 | Howell |
| 5,786,846 A | 7/1998 | Hiroaki |
| 5,787,545 A | 8/1998 | Colens |
| 5,793,365 A | 8/1998 | Tang et al. |
| 5,801,755 A | 9/1998 | Echerer |
| 5,802,494 A | 9/1998 | Kuno |
| 5,836,872 A | 11/1998 | Kenet et al. |
| 5,838,575 A | 11/1998 | Lion |
| 5,844,599 A | 12/1998 | Hildin |
| 5,857,534 A | 1/1999 | DeVault et al. |
| 5,867,494 A | 2/1999 | Krishnaswamy et al. |
| 5,867,653 A | 2/1999 | Aras et al. |
| 5,871,451 A | 2/1999 | Unger et al. |
| 5,872,922 A | 2/1999 | Hogan et al. |
| 5,999,977 A | 2/1999 | Riddle |
| 5,876,325 A | 3/1999 | Mizuno et al. |
| 5,911,036 A | 6/1999 | Wright et al. |
| 5,917,958 A | 6/1999 | Nunally et al. |
| 5,927,423 A | 7/1999 | Wada et al. |
| 5,949,758 A | 9/1999 | Kober et al. |
| 5,954,692 A | 9/1999 | Smith et al. |
| 5,959,423 A | 9/1999 | Nakanishi et al. |
| 5,961,446 A | 10/1999 | Beller et al. |
| 5,966,130 A | 10/1999 | Benman |
| 5,973,724 A | 10/1999 | Riddle |
| 5,974,446 A | 10/1999 | Sonnenreich et al. |
| 5,983,263 A | 11/1999 | Rothrock et al. |
| 5,995,119 A | 11/1999 | Cosatto et al. |
| 5,995,884 A | 11/1999 | Allen et al. |
| 6,006,946 A | 12/1999 | Williams et al. |
| 6,031,845 A | 2/2000 | Walding |
| 6,036,812 A | 3/2000 | Williams et al. |
| 6,047,259 A | 4/2000 | Campbell et al. |
| 6,091,219 A | 7/2000 | Maruo et al. |
| 6,113,343 A | 9/2000 | Goldenberg et al. |
| 6,133,944 A | 10/2000 | Braun |
| 6,135,228 A | 10/2000 | Asada et al. |
| 6,148,100 A | 11/2000 | Anderson et al. |
| 6,160,582 A | 12/2000 | Hill |
| 6,170,929 B1 | 1/2001 | Wilson et al. |
| 6,175,779 B1 | 1/2001 | Barrett |
| 6,189,034 B1 | 2/2001 | Riddle |
| 6,201,984 B1 | 3/2001 | Funda et al. |
| 6,211,903 B1 | 4/2001 | Bullister |
| 6,219,587 B1 | 4/2001 | Ahlin et al. |
| 6,232,735 B1 | 5/2001 | Baba |
| 6,233,504 B1 | 5/2001 | Das et al. |
| 6,233,735 B1 | 5/2001 | Ebihara |
| 6,250,928 B1 | 6/2001 | Poggio et al. |
| 6,256,556 B1 | 7/2001 | Zenke |
| 6,259,806 B1 | 7/2001 | Green |
| 6,259,956 B1 | 7/2001 | Myers et al. |
| 6,266,162 B1 | 7/2001 | Okamura et al. |
| 6,266,577 B1 | 7/2001 | Popp et al. |
| 6,289,263 B1 | 9/2001 | Mukherjee |

(56) References Cited

U.S. PATENT DOCUMENTS

| | | |
|---|---|---|
| 6,292,713 B1 | 9/2001 | Jouppi et al. |
| 6,292,714 B1 | 9/2001 | Okabayashi |
| 6,304,050 B1 | 10/2001 | Skaar et al. |
| 6,314,631 B1 | 11/2001 | Pryor |
| 6,317,652 B1 | 11/2001 | Osada |
| 6,317,953 B1 | 11/2001 | Pryor |
| 6,321,137 B1 | 11/2001 | De Smet |
| 6,324,184 B1 | 11/2001 | Hou et al. |
| 6,324,443 B1 | 11/2001 | Kurakake et al. |
| 6,325,756 B1 | 12/2001 | Webb et al. |
| 6,327,516 B1 | 12/2001 | Zenke |
| 6,330,486 B1 | 12/2001 | Padula |
| 6,330,493 B1 | 12/2001 | Takahashi et al. |
| 6,346,950 B1 | 2/2002 | Jouppi |
| 6,346,962 B1 | 2/2002 | Goodridge |
| 6,369,847 B1 | 4/2002 | James et al. |
| 6,373,855 B1 | 4/2002 | Downing et al. |
| 6,381,515 B1 | 4/2002 | Inoue et al. |
| 6,389,329 B1 | 5/2002 | Colens |
| 6,400,378 B1 | 6/2002 | Snook |
| 6,408,230 B2 | 6/2002 | Wada |
| 6,411,055 B1 | 6/2002 | Fujita et al. |
| 6,430,471 B1 | 8/2002 | Kintou et al. |
| 6,430,475 B2 | 8/2002 | Okamoto |
| 6,438,457 B1 | 8/2002 | Yokoo |
| 6,445,964 B1 | 9/2002 | White et al. |
| 6,449,762 B1 | 9/2002 | McElvain |
| 6,452,915 B1 | 9/2002 | Jorgensen |
| 6,457,043 B1 | 9/2002 | Kwak et al. |
| 6,459,955 B1 | 10/2002 | Bartsch et al. |
| 6,463,352 B1 | 10/2002 | Tadokoro et al. |
| 6,463,361 B1 | 10/2002 | Wang et al. |
| 6,466,844 B1 | 10/2002 | Ikeda et al. |
| 6,468,265 B1 | 10/2002 | Evans et al. |
| 6,470,235 B2 | 10/2002 | Kasuga et al. |
| 6,474,434 B1 | 11/2002 | Bech |
| 6,480,762 B1 | 11/2002 | Uchikubo et al. |
| 6,491,701 B2 | 12/2002 | Tierney |
| 6,496,099 B2 | 12/2002 | Wang et al. |
| 6,496,755 B2 | 12/2002 | Wallach et al. |
| 6,501,740 B1 | 12/2002 | Sun et al. |
| 6,507,773 B2 | 1/2003 | Parker et al. |
| 6,522,906 B1 | 2/2003 | Salisbury et al. |
| 6,523,629 B1 | 2/2003 | Buttz et al. |
| 6,526,332 B2 | 2/2003 | Sakamoto et al. |
| 6,529,620 B2 | 3/2003 | Thompson |
| 6,529,765 B1 | 3/2003 | Franck |
| 6,529,802 B1 | 3/2003 | Kawakita et al. |
| 6,532,404 B2 | 3/2003 | Colens |
| 6,535,182 B2 | 3/2003 | Stanton |
| 6,535,793 B2 | 3/2003 | Allard |
| 6,540,039 B1 | 4/2003 | Yu |
| 6,543,899 B2 | 4/2003 | Covannon et al. |
| 6,549,215 B2 | 4/2003 | Jouppi |
| 6,563,533 B1 | 5/2003 | Colby |
| 6,567,038 B1 | 5/2003 | Granot et al. |
| 6,580,246 B2 | 6/2003 | Jacobs |
| 6,581,798 B2 | 6/2003 | Liff et al. |
| 6,584,376 B1 | 6/2003 | Van Kommer |
| 6,587,750 B2 | 7/2003 | Gerbi et al. |
| 6,590,604 B1 | 7/2003 | Tucker et al. |
| 6,594,269 B1 | 7/2003 | Polcyn |
| 6,594,552 B1 | 7/2003 | Nowlin et al. |
| 6,597,392 B1 | 7/2003 | Jenkins et al. |
| 6,602,469 B1 | 8/2003 | Maus et al. |
| 6,604,019 B2 | 8/2003 | Ahlin et al. |
| 6,604,021 B2 | 8/2003 | Imai et al. |
| 6,611,120 B2 | 8/2003 | Song et al. |
| 6,643,496 B1 | 11/2003 | Shimoyama et al. |
| 6,646,677 B2 | 11/2003 | Noro et al. |
| 6,650,748 B1 | 11/2003 | Edwards et al. |
| 6,666,374 B1 | 12/2003 | Green et al. |
| 6,667,592 B2 | 12/2003 | Jacobs et al. |
| 6,674,259 B1 | 1/2004 | Norman et al. |
| 6,684,129 B2 | 1/2004 | Salisbury et al. |
| 6,691,000 B2 | 2/2004 | Nagai et al. |
| 6,693,585 B1 | 2/2004 | Macleod |
| 6,710,797 B1 | 3/2004 | McNelley et al. |
| 6,724,823 B2 | 4/2004 | Rovati et al. |
| 6,728,599 B2 | 4/2004 | Wang et al. |
| 6,763,282 B2 | 7/2004 | Glenn et al. |
| 6,764,373 B1 | 7/2004 | Osawa et al. |
| 6,769,771 B2 | 8/2004 | Trumbull |
| 6,781,606 B2 | 8/2004 | Jouppi et al. |
| 6,784,916 B2 | 8/2004 | Smith |
| 6,785,589 B2 | 8/2004 | Eggenberger et al. |
| 6,791,550 B2 | 9/2004 | Goldhor et al. |
| 6,798,753 B1 | 9/2004 | Doganata et al. |
| 6,799,065 B1 | 9/2004 | Niemeyer |
| 6,799,088 B2 | 9/2004 | Wang et al. |
| 6,804,580 B1 | 10/2004 | Stoddard et al. |
| 6,804,656 B1 | 10/2004 | Rosenfeld et al. |
| 6,810,411 B1 | 10/2004 | Coughlin et al. |
| 6,816,192 B1 | 11/2004 | Nishikawa |
| 6,816,754 B2 | 11/2004 | Mukai et al. |
| 6,836,703 B2 | 12/2004 | Wang et al. |
| 6,839,612 B2 | 1/2005 | Sanchez et al. |
| 6,840,904 B2 | 1/2005 | Goldberg |
| 6,845,297 B2 | 1/2005 | Allard |
| 6,852,107 B2 | 2/2005 | Wang et al. |
| 6,853,878 B2 | 2/2005 | Hirayama et al. |
| 6,853,880 B2 | 2/2005 | Sakagami et al. |
| 6,871,117 B2 | 3/2005 | Wang et al. |
| 6,879,879 B2 | 4/2005 | Jouppi et al. |
| 6,888,333 B2 | 5/2005 | Laby |
| 6,892,112 B2 | 5/2005 | Wang et al. |
| 6,893,267 B1 | 5/2005 | Yueh |
| 6,895,305 B2 | 5/2005 | Lathan et al. |
| 6,898,484 B2 | 5/2005 | Lemelson et al. |
| 6,914,622 B1 | 7/2005 | Smith et al. |
| 6,925,357 B2 | 8/2005 | Wang et al. |
| 6,951,535 B2 | 10/2005 | Ghodoussi et al. |
| 6,952,470 B1 | 10/2005 | Tioe |
| 6,957,712 B2 | 10/2005 | Song et al. |
| 6,958,706 B2 | 10/2005 | Chaco et al. |
| 6,965,394 B2 | 11/2005 | Gutta et al. |
| 6,990,112 B1 | 1/2006 | Brent et al. |
| 6,995,664 B1 | 2/2006 | Darling et al. |
| 7,007,235 B1 | 2/2006 | Hussein et al. |
| 7,011,538 B2 | 3/2006 | Chang |
| 7,015,934 B2 | 3/2006 | Toyama et al. |
| RE39,080 E | 4/2006 | Johnston |
| 7,030,757 B2 | 4/2006 | Matsuhira et al. |
| 7,053,578 B2 | 5/2006 | Diehl et al. |
| 7,055,210 B2 | 6/2006 | Keppler et al. |
| 7,058,689 B2 | 6/2006 | Parker et al. |
| 7,092,001 B2 | 8/2006 | Schulz |
| 7,096,090 B1 | 8/2006 | Zweig |
| 7,115,102 B2 | 10/2006 | Abbruscato |
| 7,117,067 B2 | 10/2006 | McLurkin et al. |
| 7,123,285 B2 | 10/2006 | Smith et al. |
| 7,123,974 B1 | 10/2006 | Hamilton |
| 7,123,991 B2 | 10/2006 | Graf et al. |
| 7,127,325 B2 | 10/2006 | Nagata et al. |
| 7,129,970 B2 | 10/2006 | James et al. |
| 7,133,062 B2 | 11/2006 | Castles et al. |
| 7,142,945 B2 | 11/2006 | Wang et al. |
| 7,142,947 B2 | 11/2006 | Wang et al. |
| 7,151,982 B2 | 12/2006 | Liff |
| 7,154,526 B2 | 12/2006 | Foote et al. |
| 7,155,306 B2 | 12/2006 | Haitin et al. |
| 7,156,809 B2 | 1/2007 | Quy |
| 7,158,859 B2 | 1/2007 | Wang et al. |
| 7,158,860 B2 | 1/2007 | Wang et al. |
| 7,158,861 B2 | 1/2007 | Wang et al. |
| 7,161,322 B2 | 1/2007 | Wang et al. |
| 7,162,338 B2 | 1/2007 | Goncalves et al. |
| 7,164,969 B2 | 1/2007 | Wang et al. |
| 7,164,970 B2 | 1/2007 | Wang et al. |
| 7,167,448 B2 | 1/2007 | Wookey et al. |
| 7,171,286 B2 | 1/2007 | Wang et al. |
| 7,174,238 B1 | 2/2007 | Zweig |
| 7,181,455 B2 | 2/2007 | Wookey et al. |
| 7,184,559 B2 | 2/2007 | Jouppi |

(56) References Cited

U.S. PATENT DOCUMENTS

| | | |
|---|---|---|
| 7,188,000 B2 | 3/2007 | Chiappetta et al. |
| 7,199,790 B2 | 4/2007 | Rosenberg et al. |
| 7,202,851 B2 | 4/2007 | Cunningham et al. |
| 7,206,627 B2 | 4/2007 | Abovitz et al. |
| 7,215,786 B2 | 5/2007 | Nakadai et al. |
| 7,219,364 B2 | 5/2007 | Bolle et al. |
| 7,222,000 B2 | 5/2007 | Wang et al. |
| 7,227,334 B2 | 6/2007 | Yang et al. |
| 7,256,708 B2 | 8/2007 | Rosenfeld |
| 7,262,573 B2 | 8/2007 | Wang et al. |
| 7,283,153 B2 | 10/2007 | Provost et al. |
| 7,289,883 B2 | 10/2007 | Wang et al. |
| 7,292,257 B2 | 11/2007 | Kang et al. |
| 7,292,912 B2 | 11/2007 | Way et al. |
| 7,305,114 B2 | 12/2007 | Wolff et al. |
| 7,317,685 B1 | 1/2008 | Flott et al. |
| 7,321,807 B2 | 1/2008 | Laski |
| 7,332,890 B2 | 2/2008 | Cohen et al. |
| 7,333,642 B2 | 2/2008 | Green |
| 7,346,429 B2 | 3/2008 | Goldenberg et al. |
| 7,352,153 B2 | 4/2008 | Yan |
| 7,363,121 B1 | 4/2008 | Chen et al. |
| 7,382,399 B1 | 6/2008 | McCall |
| 7,386,730 B2 | 6/2008 | Uchikubo |
| 7,391,432 B2 | 6/2008 | Terada |
| 7,400,578 B2 | 7/2008 | Guthrie et al. |
| 7,404,140 B2 | 7/2008 | O'Rourke |
| 7,421,470 B2 | 9/2008 | Ludwig et al. |
| 7,430,209 B2 | 9/2008 | Porter |
| 7,432,949 B2 | 10/2008 | Remy et al. |
| 7,433,921 B2 | 10/2008 | Ludwig et al. |
| 7,441,953 B2 | 10/2008 | Banks |
| 7,467,211 B1 | 12/2008 | Herman et al. |
| 7,483,867 B2 | 1/2009 | Ansari et al. |
| 7,492,731 B2 | 2/2009 | Hagendorf |
| 7,510,428 B2 | 3/2009 | Obata et al. |
| 7,523,069 B1 | 4/2009 | Friedl et al. |
| 7,525,281 B2 | 4/2009 | Koyanagi et al. |
| 7,535,486 B2 | 5/2009 | Motomura et al. |
| 7,557,758 B2 | 7/2009 | Rofougaran |
| 7,587,260 B2 | 9/2009 | Bruemmer et al. |
| 7,587,512 B2 | 9/2009 | Ta et al. |
| 7,590,060 B2 | 9/2009 | Miceli |
| 7,593,030 B2 | 9/2009 | Way et al. |
| 7,599,290 B2 | 10/2009 | Dos Remedios et al. |
| 7,624,166 B2 | 11/2009 | Foote et al. |
| 7,630,314 B2 | 12/2009 | Dos Remedios et al. |
| 7,631,833 B1 | 12/2009 | Ghaleb et al. |
| 7,643,051 B2 | 1/2010 | Sandberg et al. |
| 7,647,320 B2 | 1/2010 | Mok et al. |
| 7,657,560 B1 | 2/2010 | Dirienzo |
| 7,680,038 B1 | 3/2010 | Gourlay |
| 7,693,757 B2 | 4/2010 | Zimmerman |
| 7,698,432 B2 | 4/2010 | Short et al. |
| 7,703,113 B2 | 4/2010 | Dawson |
| 7,719,229 B2 | 5/2010 | Kaneko et al. |
| 7,737,993 B2 | 6/2010 | Kaasila et al. |
| 7,739,383 B1 | 6/2010 | Short et al. |
| 7,756,614 B2 | 7/2010 | Jouppi |
| 7,761,185 B2 | 7/2010 | Wang et al. |
| 7,769,492 B2 | 8/2010 | Wang et al. |
| 7,769,705 B1 | 8/2010 | Luechtefeld |
| 7,774,158 B2 | 8/2010 | Domingues Goncalves et al. |
| 7,813,836 B2 | 10/2010 | Wang et al. |
| 7,831,575 B2 | 11/2010 | Trossell et al. |
| 7,835,775 B2 | 11/2010 | Sawayama et al. |
| 7,860,680 B2 | 12/2010 | Arms et al. |
| 7,861,366 B2 | 1/2011 | Hahm et al. |
| 7,885,822 B2 | 2/2011 | Akers et al. |
| 7,890,382 B2 | 2/2011 | Robb et al. |
| 7,912,583 B2 | 3/2011 | Gutmann et al. |
| RE42,288 E | 4/2011 | Degioanni |
| 7,924,323 B2 | 4/2011 | Walker et al. |
| 7,949,616 B2 | 5/2011 | Levy et al. |
| 7,956,894 B2 | 6/2011 | Akers et al. |
| 7,957,837 B2 | 6/2011 | Ziegler et al. |
| 7,982,763 B2 | 7/2011 | King |
| 7,982,769 B2 | 7/2011 | Jenkins et al. |
| 7,987,069 B2 | 7/2011 | Rodgers et al. |
| 8,077,963 B2 | 12/2011 | Wang et al. |
| 8,116,910 B2 | 2/2012 | Walters et al. |
| 8,126,960 B2 | 2/2012 | Obradovich et al. |
| 8,170,241 B2 | 5/2012 | Roe et al. |
| 8,179,418 B2 | 5/2012 | Wright et al. |
| 8,180,486 B2 | 5/2012 | Saito et al. |
| 8,209,051 B2 | 6/2012 | Yulun et al. |
| 8,212,533 B2 | 7/2012 | Ota |
| 8,265,793 B2 | 9/2012 | Cross et al. |
| 8,287,522 B2 | 10/2012 | Moses et al. |
| 8,292,807 B2 | 10/2012 | Perkins et al. |
| 8,320,534 B2 | 11/2012 | Kim et al. |
| 8,340,654 B2 * | 12/2012 | Bratton .................. H04N 5/232 348/211.11 |
| 8,340,819 B2 | 12/2012 | Mangaser et al. |
| 8,348,675 B2 | 1/2013 | Dohrmann |
| 8,374,171 B2 | 2/2013 | Cho et al. |
| 8,400,491 B1 | 3/2013 | Panpaliya et al. |
| 8,401,275 B2 | 3/2013 | Wang et al. |
| 8,423,284 B2 | 4/2013 | O'Shea |
| 8,451,731 B1 | 5/2013 | Lee et al. |
| 8,463,435 B2 | 6/2013 | Herzog et al. |
| 8,503,340 B1 | 8/2013 | Xu |
| 8,515,577 B2 | 8/2013 | Wang et al. |
| 8,527,094 B2 | 9/2013 | Kumar et al. |
| 8,532,860 B2 | 9/2013 | Daly |
| 8,610,786 B2 | 12/2013 | Ortiz |
| 8,612,051 B2 | 12/2013 | Norman et al. |
| 8,639,797 B1 | 1/2014 | Pan et al. |
| 8,670,017 B2 | 3/2014 | Stuart et al. |
| 8,726,454 B2 | 5/2014 | Gilbert, Jr. et al. |
| 8,836,751 B2 | 9/2014 | Ballantyne et al. |
| 8,849,679 B2 | 9/2014 | Wang et al. |
| 8,849,680 B2 | 9/2014 | Wright et al. |
| 8,861,750 B2 | 10/2014 | Roe et al. |
| 8,897,920 B2 | 11/2014 | Wang et al. |
| 8,902,278 B2 | 12/2014 | Pinter et al. |
| 2001/0002448 A1 | 5/2001 | Wilson |
| 2001/0010053 A1 | 7/2001 | Ben-Shachar et al. |
| 2001/0020200 A1 | 9/2001 | Das et al. |
| 2001/0034475 A1 | 10/2001 | Flach et al. |
| 2001/0034544 A1 | 10/2001 | Mo |
| 2001/0037163 A1 | 11/2001 | Allard |
| 2001/0048464 A1 | 12/2001 | Barnett |
| 2001/0051881 A1 | 12/2001 | Filler |
| 2001/0054071 A1 | 12/2001 | Loeb |
| 2001/0055373 A1 | 12/2001 | Yamashita |
| 2002/0015296 A1 | 2/2002 | Howell et al. |
| 2002/0027597 A1 | 3/2002 | Sachau |
| 2002/0027652 A1 | 3/2002 | Paromtchik et al. |
| 2002/0033880 A1 | 3/2002 | Sul et al. |
| 2002/0038168 A1 | 3/2002 | Kasuga et al. |
| 2002/0044201 A1 | 4/2002 | Alexander et al. |
| 2002/0049517 A1 | 4/2002 | Ruffner |
| 2002/0055917 A1 | 5/2002 | Muraca |
| 2002/0057279 A1 | 5/2002 | Jouppi |
| 2002/0058929 A1 | 5/2002 | Green |
| 2002/0059587 A1 | 5/2002 | Cofano et al. |
| 2002/0063726 A1 | 5/2002 | Jouppi |
| 2002/0073429 A1 | 6/2002 | Beane et al. |
| 2002/0082498 A1 | 6/2002 | Wendt et al. |
| 2002/0085030 A1 | 7/2002 | Ghani |
| 2002/0095238 A1 | 7/2002 | Ahlin et al. |
| 2002/0095239 A1 | 7/2002 | Wallach et al. |
| 2002/0098879 A1 | 7/2002 | Rheey |
| 2002/0104094 A1 | 8/2002 | Alexander et al. |
| 2002/0106998 A1 | 8/2002 | Presley et al. |
| 2002/0109770 A1 | 8/2002 | Terada |
| 2002/0109775 A1 | 8/2002 | White et al. |
| 2002/0111988 A1 | 8/2002 | Sato |
| 2002/0120362 A1 | 8/2002 | Lathan et al. |
| 2002/0128985 A1 | 9/2002 | Greenwald |
| 2002/0130950 A1 | 9/2002 | James et al. |
| 2002/0133062 A1 | 9/2002 | Arling et al. |
| 2002/0141595 A1 | 10/2002 | Jouppi |

(56) References Cited

U.S. PATENT DOCUMENTS

| | | |
|---|---|---|
| 2002/0143923 A1 | 10/2002 | Alexander |
| 2002/0177925 A1 | 11/2002 | Onishi et al. |
| 2002/0183894 A1 | 12/2002 | Wang |
| 2002/0184674 A1 | 12/2002 | Xi et al. |
| 2002/0186243 A1 | 12/2002 | Ellis et al. |
| 2003/0021107 A1 | 1/2003 | Howell et al. |
| 2003/0030397 A1 | 2/2003 | Simmons |
| 2003/0048481 A1 | 3/2003 | Kobayashi et al. |
| 2003/0050733 A1 | 3/2003 | Wang et al. |
| 2003/0050734 A1 | 3/2003 | Lapham |
| 2003/0060808 A1 | 3/2003 | Wilk |
| 2003/0063600 A1 | 4/2003 | Noma et al. |
| 2003/0069752 A1 | 4/2003 | Ledain et al. |
| 2003/0080901 A1 | 5/2003 | Piotrowski |
| 2003/0100892 A1 | 5/2003 | Morley et al. |
| 2003/0104806 A1 | 6/2003 | Ruef et al. |
| 2003/0112823 A1 | 6/2003 | Collins et al. |
| 2003/0114962 A1 | 6/2003 | Niemeyer et al. |
| 2003/0120714 A1 | 6/2003 | Wolff et al. |
| 2003/0126361 A1 | 7/2003 | Slater et al. |
| 2003/0135097 A1 | 7/2003 | Wiederhold et al. |
| 2003/0135203 A1 | 7/2003 | Wang et al. |
| 2003/0144579 A1 | 7/2003 | Buss |
| 2003/0144649 A1 | 7/2003 | Ghodoussi et al. |
| 2003/0151658 A1 | 8/2003 | Smith |
| 2003/0152145 A1 | 8/2003 | Kawakita |
| 2003/0171710 A1 | 9/2003 | Bassuk et al. |
| 2003/0174285 A1 | 9/2003 | Trumbull |
| 2003/0180697 A1 | 9/2003 | Kim et al. |
| 2003/0195662 A1 | 10/2003 | Wang et al. |
| 2003/0199000 A1 | 10/2003 | Valkirs et al. |
| 2003/0206242 A1 | 11/2003 | Choi et al. |
| 2003/0212472 A1 | 11/2003 | McKee |
| 2003/0216833 A1 | 11/2003 | Mukai et al. |
| 2003/0216834 A1 | 11/2003 | Allard |
| 2003/0220541 A1 | 11/2003 | Salisbury et al. |
| 2003/0220715 A1 | 11/2003 | William et al. |
| 2003/0231244 A1 | 12/2003 | Bonilla et al. |
| 2003/0232649 A1 | 12/2003 | Gizis |
| 2003/0236590 A1 | 12/2003 | Park et al. |
| 2004/0001197 A1 | 1/2004 | Ko et al. |
| 2004/0001676 A1 | 1/2004 | Colgan et al. |
| 2004/0008138 A1 | 1/2004 | Hockley, Jr. et al. |
| 2004/0010344 A1 | 1/2004 | Hiratsuka |
| 2004/0012362 A1 | 1/2004 | Tsurumi |
| 2004/0013295 A1 | 1/2004 | Sabe et al. |
| 2004/0017475 A1 | 1/2004 | Akers et al. |
| 2004/0019406 A1 | 1/2004 | Wang et al. |
| 2004/0024490 A1 | 2/2004 | McLurkin et al. |
| 2004/0041904 A1 | 3/2004 | Lapalme et al. |
| 2004/0065073 A1 | 4/2004 | Nash |
| 2004/0068657 A1 | 4/2004 | Alexander et al. |
| 2004/0078219 A1 | 4/2004 | Kaylor et al. |
| 2004/0080610 A1 | 4/2004 | James et al. |
| 2004/0088077 A1 | 5/2004 | Jouppi et al. |
| 2004/0088078 A1 | 5/2004 | Jouppi et al. |
| 2004/0093409 A1 | 5/2004 | Thompson et al. |
| 2004/0095516 A1 | 5/2004 | Rohlicek |
| 2004/0098167 A1 | 5/2004 | Yi et al. |
| 2004/0102167 A1 | 5/2004 | Shim et al. |
| 2004/0107254 A1 | 6/2004 | Ludwig et al. |
| 2004/0107255 A1 | 6/2004 | Ludwig et al. |
| 2004/0117065 A1 | 6/2004 | Wang et al. |
| 2004/0117067 A1 | 6/2004 | Jouppi |
| 2004/0123158 A1 | 6/2004 | Roskind |
| 2004/0135879 A1 | 7/2004 | Stacy et al. |
| 2004/0138547 A1 | 7/2004 | Wang et al. |
| 2004/0143421 A1 | 7/2004 | Wang et al. |
| 2004/0148638 A1 | 7/2004 | Weisman et al. |
| 2004/0150725 A1 | 8/2004 | Taguchi |
| 2004/0153211 A1 | 8/2004 | Kamoto et al. |
| 2004/0157612 A1 | 8/2004 | Kim |
| 2004/0162637 A1 | 8/2004 | Wang et al. |
| 2004/0167666 A1 | 8/2004 | Wang et al. |
| 2004/0167668 A1 | 8/2004 | Wang et al. |
| 2004/0168148 A1 | 8/2004 | Goncalves et al. |
| 2004/0170300 A1 | 9/2004 | Jouppi |
| 2004/0172301 A1 | 9/2004 | Mihai et al. |
| 2004/0172306 A1 | 9/2004 | Wohl et al. |
| 2004/0174129 A1 | 9/2004 | Wang et al. |
| 2004/0175684 A1 | 9/2004 | Kaasa et al. |
| 2004/0179714 A1 | 9/2004 | Jouppi |
| 2004/0186623 A1 | 9/2004 | Dooley et al. |
| 2004/0189700 A1 | 9/2004 | Mandavilli et al. |
| 2004/0201602 A1 | 10/2004 | Mody et al. |
| 2004/0205664 A1 | 10/2004 | Prendergast |
| 2004/0215490 A1 | 10/2004 | Duchon et al. |
| 2004/0218099 A1 | 11/2004 | Washington |
| 2004/0222638 A1 | 11/2004 | Bednyak |
| 2004/0224676 A1 | 11/2004 | Iseki |
| 2004/0230340 A1 | 11/2004 | Fukuchi et al. |
| 2004/0241981 A1 | 12/2004 | Dothan et al. |
| 2004/0260790 A1 | 12/2004 | Balloni et al. |
| 2005/0003330 A1 | 1/2005 | Asgarinejad et al. |
| 2005/0004708 A1 | 1/2005 | Goldenberg et al. |
| 2005/0007445 A1 | 1/2005 | Foote et al. |
| 2005/0013149 A1 | 1/2005 | Trossell |
| 2005/0021182 A1 | 1/2005 | Wang |
| 2005/0021183 A1 | 1/2005 | Wang et al. |
| 2005/0021187 A1 | 1/2005 | Wang et al. |
| 2005/0021309 A1 | 1/2005 | Alexander et al. |
| 2005/0024485 A1 | 2/2005 | Castles et al. |
| 2005/0027567 A1 | 2/2005 | Taha |
| 2005/0027794 A1 | 2/2005 | Decker |
| 2005/0028221 A1 | 2/2005 | Liu et al. |
| 2005/0035862 A1 | 2/2005 | Wildman et al. |
| 2005/0038416 A1 | 2/2005 | Wang et al. |
| 2005/0038564 A1 | 2/2005 | Burick et al. |
| 2005/0049898 A1 | 3/2005 | Hirakawa |
| 2005/0052527 A1 | 3/2005 | Remy et al. |
| 2005/0060211 A1 | 3/2005 | Xiao et al. |
| 2005/0065435 A1 | 3/2005 | Rauch et al. |
| 2005/0065438 A1 | 3/2005 | Miller |
| 2005/0065659 A1 | 3/2005 | Tanaka |
| 2005/0065813 A1 | 3/2005 | Mishelevich et al. |
| 2005/0071046 A1 | 3/2005 | Miyazaki et al. |
| 2005/0073575 A1 | 4/2005 | Thacher et al. |
| 2005/0078816 A1 | 4/2005 | Sekiguchi et al. |
| 2005/0083011 A1 | 4/2005 | Yang et al. |
| 2005/0099493 A1 | 5/2005 | Chew |
| 2005/0104964 A1 | 5/2005 | Bovyrin et al. |
| 2005/0110867 A1 | 5/2005 | Schulz |
| 2005/0122390 A1 | 6/2005 | Wang et al. |
| 2005/0125083 A1 | 6/2005 | Kiko |
| 2005/0125098 A1 | 6/2005 | Wang et al. |
| 2005/0149364 A1 | 7/2005 | Ombrellaro |
| 2005/0152447 A1 | 7/2005 | Jouppi et al. |
| 2005/0152565 A1 | 7/2005 | Jouppi et al. |
| 2005/0154265 A1 | 7/2005 | Miro et al. |
| 2005/0168568 A1 | 8/2005 | Jouppi |
| 2005/0182322 A1 | 8/2005 | Grispo |
| 2005/0192721 A1 | 9/2005 | Jouppi |
| 2005/0204438 A1 | 9/2005 | Wang et al. |
| 2005/0212478 A1 | 9/2005 | Takenaka |
| 2005/0219356 A1 | 10/2005 | Smith et al. |
| 2005/0225634 A1 | 10/2005 | Brunetti et al. |
| 2005/0231156 A1 | 10/2005 | Yan |
| 2005/0231586 A1 | 10/2005 | Rodman et al. |
| 2005/0232647 A1 | 10/2005 | Takenaka |
| 2005/0234592 A1 | 10/2005 | McGee et al. |
| 2005/0264649 A1 | 12/2005 | Chang et al. |
| 2005/0267826 A1 | 12/2005 | Levy et al. |
| 2005/0283414 A1 | 12/2005 | Fernandes et al. |
| 2005/0286759 A1 | 12/2005 | Zitnick et al. |
| 2006/0007943 A1 | 1/2006 | Fellman |
| 2006/0010028 A1 | 1/2006 | Sorensen |
| 2006/0013263 A1 | 1/2006 | Fellman |
| 2006/0013469 A1 | 1/2006 | Wang et al. |
| 2006/0013488 A1 | 1/2006 | Inoue |
| 2006/0014388 A1 | 1/2006 | Lur et al. |
| 2006/0020694 A1 | 1/2006 | Nag et al. |
| 2006/0029065 A1 | 2/2006 | Fellman |
| 2006/0047365 A1 | 3/2006 | Ghodoussi et al. |
| 2006/0048286 A1 | 3/2006 | Donato |

(56) References Cited

U.S. PATENT DOCUMENTS

| | | |
|---|---|---|
| 2006/0052676 A1 | 3/2006 | Wang et al. |
| 2006/0052684 A1 | 3/2006 | Takahashi et al. |
| 2006/0056655 A1 | 3/2006 | Wen et al. |
| 2006/0056837 A1 | 3/2006 | Vapaakoski |
| 2006/0064212 A1 | 3/2006 | Thorne |
| 2006/0066609 A1 | 3/2006 | Todice et al. |
| 2006/0071797 A1 | 4/2006 | Rosenfeld et al. |
| 2006/0074525 A1 | 4/2006 | Close et al. |
| 2006/0074719 A1 | 4/2006 | Horner |
| 2006/0082642 A1 | 4/2006 | Wang et al. |
| 2006/0087746 A1 | 4/2006 | Lipow |
| 2006/0095158 A1 | 5/2006 | Lee et al. |
| 2006/0095170 A1 | 5/2006 | Yang et al. |
| 2006/0098573 A1 | 5/2006 | Beer et al. |
| 2006/0103659 A1 | 5/2006 | Karandikar et al. |
| 2006/0104279 A1 | 5/2006 | Fellman et al. |
| 2006/0106493 A1 | 5/2006 | Niemeyer et al. |
| 2006/0122482 A1 | 6/2006 | Mariotti et al. |
| 2006/0125356 A1 | 6/2006 | Meek et al. |
| 2006/0142983 A1 | 6/2006 | Sorensen et al. |
| 2006/0149418 A1 | 7/2006 | Anvari |
| 2006/0161136 A1 | 7/2006 | Anderson et al. |
| 2006/0161303 A1 | 7/2006 | Wang et al. |
| 2006/0164546 A1 | 7/2006 | Adachi et al. |
| 2006/0171515 A1 | 8/2006 | Hintermeister et al. |
| 2006/0173708 A1* | 8/2006 | Vining ............... A61B 5/0002 705/2 |
| 2006/0173712 A1 | 8/2006 | Joubert |
| 2006/0178559 A1 | 8/2006 | Kumar et al. |
| 2006/0178776 A1 | 8/2006 | Feingold et al. |
| 2006/0178777 A1 | 8/2006 | Park et al. |
| 2006/0189393 A1 | 8/2006 | Edery |
| 2006/0195569 A1 | 8/2006 | Barker |
| 2006/0224781 A1 | 10/2006 | Tsao et al. |
| 2006/0247045 A1 | 11/2006 | Jeong et al. |
| 2006/0259193 A1 | 11/2006 | Wang et al. |
| 2006/0268704 A1 | 11/2006 | Ansari et al. |
| 2006/0271238 A1 | 11/2006 | Choi et al. |
| 2006/0271400 A1 | 11/2006 | Clements et al. |
| 2006/0293788 A1 | 12/2006 | Pogodin |
| 2007/0021871 A1 | 1/2007 | Wang et al. |
| 2007/0025711 A1 | 2/2007 | Marcus |
| 2007/0046237 A1 | 3/2007 | Lakshmanan et al. |
| 2007/0050937 A1 | 3/2007 | Song et al. |
| 2007/0064092 A1 | 3/2007 | Sandbeg et al. |
| 2007/0078566 A1 | 4/2007 | Wang et al. |
| 2007/0093279 A1 | 4/2007 | Janik |
| 2007/0112700 A1 | 5/2007 | Den et al. |
| 2007/0116152 A1 | 5/2007 | Thesling |
| 2007/0117516 A1 | 5/2007 | Saidi et al. |
| 2007/0120965 A1 | 5/2007 | Sandberg et al. |
| 2007/0122783 A1 | 5/2007 | Habashi |
| 2007/0133407 A1 | 6/2007 | Choi et al. |
| 2007/0135967 A1 | 6/2007 | Jung et al. |
| 2007/0142964 A1 | 6/2007 | Abramson |
| 2007/0170886 A1 | 7/2007 | Plishner |
| 2007/0176060 A1 | 8/2007 | White et al. |
| 2007/0192910 A1 | 8/2007 | Vu et al. |
| 2007/0197896 A1 | 8/2007 | Moll et al. |
| 2007/0198128 A1 | 8/2007 | Ziegler et al. |
| 2007/0198130 A1 | 8/2007 | Wang et al. |
| 2007/0199108 A1 | 8/2007 | Angle et al. |
| 2007/0216347 A1 | 9/2007 | Kaneko et al. |
| 2007/0226949 A1 | 10/2007 | Hahm et al. |
| 2007/0250212 A1 | 10/2007 | Halloran et al. |
| 2007/0255706 A1 | 11/2007 | Iketani et al. |
| 2007/0262884 A1 | 11/2007 | Goncalves et al. |
| 2007/0273751 A1 | 11/2007 | Sachau |
| 2007/0290040 A1 | 12/2007 | Wurman et al. |
| 2007/0291109 A1 | 12/2007 | Wang et al. |
| 2007/0291128 A1 | 12/2007 | Wang et al. |
| 2008/0009695 A1* | 1/2008 | Mejia ............... A61B 5/0002 600/407 |
| 2008/0009969 A1 | 1/2008 | Bruemmer et al. |
| 2008/0011904 A1 | 1/2008 | Cepollina et al. |
| 2008/0027591 A1 | 1/2008 | Lenser et al. |
| 2008/0033641 A1 | 2/2008 | Medalia |
| 2008/0045804 A1 | 2/2008 | Williams |
| 2008/0051985 A1 | 2/2008 | D'Andrea et al. |
| 2008/0065268 A1 | 3/2008 | Wang et al. |
| 2008/0082211 A1 | 4/2008 | Wang et al. |
| 2008/0086241 A1 | 4/2008 | Phillips et al. |
| 2008/0091340 A1 | 4/2008 | Milstein et al. |
| 2008/0126132 A1 | 5/2008 | Warner et al. |
| 2008/0133052 A1 | 6/2008 | Jones et al. |
| 2008/0161969 A1 | 7/2008 | Lee et al. |
| 2008/0174570 A1 | 7/2008 | Jobs et al. |
| 2008/0201016 A1 | 8/2008 | Finlay |
| 2008/0201017 A1 | 8/2008 | Wang et al. |
| 2008/0215987 A1 | 9/2008 | Alexander et al. |
| 2008/0229531 A1 | 9/2008 | Takida |
| 2008/0232763 A1 | 9/2008 | Brady |
| 2008/0255703 A1 | 10/2008 | Wang et al. |
| 2008/0263451 A1 | 10/2008 | Portele et al. |
| 2008/0263628 A1 | 10/2008 | Norman et al. |
| 2008/0267069 A1 | 10/2008 | Thielman et al. |
| 2008/0269949 A1 | 10/2008 | Norman et al. |
| 2008/0281467 A1 | 11/2008 | Pinter |
| 2008/0306375 A1 | 12/2008 | Sayler et al. |
| 2009/0030552 A1 | 1/2009 | Nakadai et al. |
| 2009/0044334 A1 | 2/2009 | Parsell et al. |
| 2009/0049640 A1 | 2/2009 | Lee et al. |
| 2009/0055023 A1 | 2/2009 | Walters et al. |
| 2009/0070135 A1 | 3/2009 | Parida et al. |
| 2009/0086209 A1 | 4/2009 | Thapa |
| 2009/0102919 A1 | 4/2009 | Zamierowski et al. |
| 2009/0105882 A1 | 4/2009 | Wang et al. |
| 2009/0106679 A1 | 4/2009 | Anzures et al. |
| 2009/0122699 A1 | 5/2009 | Alperovitch et al. |
| 2009/0125147 A1 | 5/2009 | Wang et al. |
| 2009/0144425 A1 | 6/2009 | Marr et al. |
| 2009/0164255 A1 | 6/2009 | Menschik et al. |
| 2009/0164657 A1 | 6/2009 | Li et al. |
| 2009/0171170 A1 | 7/2009 | Li et al. |
| 2009/0177323 A1 | 7/2009 | Ziegler et al. |
| 2009/0177641 A1 | 7/2009 | Raghavan |
| 2009/0237317 A1 | 9/2009 | Rofougaran |
| 2009/0240371 A1 | 9/2009 | Wang et al. |
| 2009/0248200 A1 | 10/2009 | Root |
| 2009/0259339 A1 | 10/2009 | Wright et al. |
| 2010/0010672 A1 | 1/2010 | Wang et al. |
| 2010/0010673 A1 | 1/2010 | Wang et al. |
| 2010/0017046 A1 | 1/2010 | Cheung et al. |
| 2010/0019715 A1 | 1/2010 | Roe et al. |
| 2010/0026239 A1 | 2/2010 | Li et al. |
| 2010/0030578 A1 | 2/2010 | Siddique et al. |
| 2010/0051596 A1 | 3/2010 | Diedrick et al. |
| 2010/0063848 A1 | 3/2010 | Kremer et al. |
| 2010/0066804 A1 | 3/2010 | Shoemake et al. |
| 2010/0070079 A1 | 3/2010 | Mangaser et al. |
| 2010/0073490 A1 | 3/2010 | Wang et al. |
| 2010/0076600 A1 | 3/2010 | Cross et al. |
| 2010/0085874 A1 | 4/2010 | Noy et al. |
| 2010/0088232 A1 | 4/2010 | Gale |
| 2010/0115418 A1 | 5/2010 | Wang et al. |
| 2010/0116566 A1 | 5/2010 | Ohm et al. |
| 2010/0131103 A1 | 5/2010 | Herzog et al. |
| 2010/0145479 A1 | 6/2010 | Griffiths |
| 2010/0157825 A1 | 6/2010 | Anderlind et al. |
| 2010/0171826 A1 | 7/2010 | Hamilton et al. |
| 2010/0191375 A1 | 7/2010 | Wright et al. |
| 2010/0228249 A1 | 9/2010 | Mohr et al. |
| 2010/0268383 A1 | 10/2010 | Wang et al. |
| 2010/0278086 A1 | 11/2010 | Pochiraju et al. |
| 2010/0286905 A1 | 11/2010 | Goncalves et al. |
| 2010/0301679 A1 | 12/2010 | Murray et al. |
| 2010/0304731 A1* | 12/2010 | Bratton ............... H04N 5/232 455/420 |
| 2010/0323783 A1 | 12/2010 | Nonaka et al. |
| 2011/0022705 A1 | 1/2011 | Yellamraju et al. |
| 2011/0050841 A1 | 3/2011 | Wang et al. |
| 2011/0071675 A1 | 3/2011 | Wells et al. |
| 2011/0071702 A1 | 3/2011 | Wang et al. |
| 2011/0072114 A1 | 3/2011 | Hoffert et al. |

(56) References Cited

U.S. PATENT DOCUMENTS

| | | |
|---|---|---|
| 2011/0153198 A1 | 6/2011 | Kokkas et al. |
| 2011/0172822 A1 | 7/2011 | Ziegler et al. |
| 2011/0187875 A1 | 8/2011 | Sanchez et al. |
| 2011/0190930 A1 | 8/2011 | Hanrahan et al. |
| 2011/0193949 A1 | 8/2011 | Nambakam et al. |
| 2011/0195701 A1 | 8/2011 | Cook et al. |
| 2011/0213210 A1 | 9/2011 | Temby et al. |
| 2011/0218674 A1 | 9/2011 | Stuart et al. |
| 2011/0245973 A1 | 10/2011 | Wang et al. |
| 2011/0280551 A1 | 11/2011 | Sammon |
| 2011/0292193 A1 | 12/2011 | Wang et al. |
| 2011/0301759 A1 | 12/2011 | Wang et al. |
| 2011/0306400 A1 | 12/2011 | Nguyen |
| 2012/0023506 A1 | 1/2012 | Maeckel et al. |
| 2012/0036484 A1 | 2/2012 | Zhang et al. |
| 2012/0059946 A1 | 3/2012 | Wang |
| 2012/0072023 A1 | 3/2012 | Ota |
| 2012/0072024 A1 | 3/2012 | Wang et al. |
| 2012/0092157 A1 | 4/2012 | Tran |
| 2012/0095352 A1 | 4/2012 | Tran |
| 2012/0113856 A1 | 5/2012 | Krishnaswamy |
| 2012/0191246 A1 | 7/2012 | Roe et al. |
| 2012/0191464 A1 | 7/2012 | Stuart et al. |
| 2012/0203731 A1 | 8/2012 | Nelson et al. |
| 2012/0291809 A1 | 11/2012 | Kuhe et al. |
| 2013/0250938 A1 | 9/2013 | Anandakumar et al. |
| 2014/0047022 A1 | 2/2014 | Chan et al. |
| 2014/0085543 A1 | 3/2014 | Hartley et al. |
| 2014/0135990 A1 | 5/2014 | Stuart et al. |
| 2014/0139616 A1 | 5/2014 | Pinter et al. |
| 2014/0155755 A1 | 6/2014 | Pinter et al. |

FOREIGN PATENT DOCUMENTS

| | | |
|---|---|---|
| CN | 1404695 A | 3/2003 |
| CN | 1554193 A | 12/2004 |
| CN | 1554985 A | 12/2004 |
| CN | 1561923 A | 1/2005 |
| CN | 1743144 A | 3/2006 |
| CN | 101049017 A | 10/2007 |
| CN | 101106939 A | 1/2008 |
| CN | 101151614 A | 3/2008 |
| CN | 100407729 C | 7/2008 |
| CN | 101390098 A | 3/2009 |
| CN | 101507260 A | 8/2009 |
| CN | 101730894 A | 6/2010 |
| CN | 101866396 A | 10/2010 |
| CN | 101978365 A | 2/2011 |
| CN | 102203759 A | 9/2011 |
| CN | 101106939 B | 11/2011 |
| EP | 92/466492 A2 | 1/1992 |
| EP | 92/488673 A2 | 1/1992 |
| EP | 466492 A2 | 1/1992 |
| EP | 488673 A2 | 6/1992 |
| EP | 0981905 B1 | 1/2002 |
| EP | 1262142 A2 | 12/2002 |
| EP | 1304872 A1 | 4/2003 |
| EP | 1536660 A2 | 6/2005 |
| EP | 1573406 A2 | 9/2005 |
| EP | 2005/1594660 A2 | 11/2005 |
| EP | 1594660 A2 | 11/2005 |
| EP | 1763243 A2 | 3/2007 |
| EP | 1791464 A2 | 6/2007 |
| EP | 1800476 A2 | 6/2007 |
| EP | 1819108 A2 | 8/2007 |
| EP | 1856644 A2 | 11/2007 |
| EP | 1536660 A3 | 4/2008 |
| EP | 1928310 A2 | 6/2008 |
| EP | 1232610 B1 | 1/2009 |
| EP | 2027716 A2 | 2/2009 |
| EP | 2145274 A1 | 1/2010 |
| EP | 2214111 A2 | 8/2010 |
| EP | 2263158 | 12/2010 |
| EP | 2300930 | 3/2011 |
| EP | 2011/2342651 A2 | 7/2011 |
| GB | 2431261 A | 4/2007 |
| JP | 07-194609 A | 8/1995 |
| JP | 07213753 A | 8/1995 |
| JP | 07248823 A | 9/1995 |
| JP | 07257422 A | 10/1995 |
| JP | 08084328 A | 3/1996 |
| JP | 8320727 A | 12/1996 |
| JP | 09267276 A | 10/1997 |
| JP | 10079097 A | 3/1998 |
| JP | 10288689 A | 10/1998 |
| JP | 11220706 A | 8/1999 |
| JP | 00032319 A | 1/2000 |
| JP | 049800 A | 2/2000 |
| JP | 079587 A | 3/2000 |
| JP | 2000-196876 A | 7/2000 |
| JP | 196876 A | 7/2000 |
| JP | 00188124 A | 4/2001 |
| JP | 125641 A | 5/2001 |
| JP | 01147718 A | 5/2001 |
| JP | 2001-188124 A | 7/2001 |
| JP | 179663 A | 7/2001 |
| JP | 01198865 A | 7/2001 |
| JP | 01198868 A | 7/2001 |
| JP | 01199356 A | 7/2001 |
| JP | 02000574 A | 1/2002 |
| JP | 046088 A | 2/2002 |
| JP | 00235423 A | 2/2002 |
| JP | 2002/112970 A | 4/2002 |
| JP | 2002/101333 A | 5/2002 |
| JP | 2002-235423 A | 8/2002 |
| JP | 02305743 A | 10/2002 |
| JP | 2002-321180 A | 11/2002 |
| JP | 02355779 A | 12/2002 |
| JP | 2004-181229 A | 7/2004 |
| JP | 2004-524824 T | 8/2004 |
| JP | 524824 T | 8/2004 |
| JP | 261941 A | 9/2004 |
| JP | 2004/289379 A | 10/2004 |
| JP | 028066 A | 2/2005 |
| JP | 2005/059170 | 3/2005 |
| JP | 2005-111083 A | 4/2005 |
| JP | 2006/508806 A | 3/2006 |
| JP | 2006109094 A | 4/2006 |
| JP | 2006/224294 A | 8/2006 |
| JP | 2006/246438 A | 9/2006 |
| JP | 2007-007040 A | 1/2007 |
| JP | 2007/081646 A | 3/2007 |
| JP | 2007-232208 A | 9/2007 |
| JP | 2007-316966 A | 12/2007 |
| JP | 2009-125133 A | 6/2009 |
| JP | 2010/064154 A | 3/2010 |
| JP | 2010/532109 A | 9/2010 |
| JP | 246954 | 11/2010 |
| KR | 2006/0037979 A | 5/2006 |
| KR | 2009/0012542 A | 2/2009 |
| KR | 0019479 A | 2/2010 |
| KR | 0139037 | 12/2010 |
| WO | WO-06690 A1 | 4/1993 |
| WO | 1997/042761 A1 | 11/1997 |
| WO | WO-051078 A1 | 11/1998 |
| WO | WO-067067 | 12/1999 |
| WO | 2000/025516 A1 | 5/2000 |
| WO | WO-033726 | 6/2000 |
| WO | 2001/031861 A1 | 5/2001 |
| WO | WO-077745 A1 | 9/2003 |
| WO | 2004/012018 A2 | 2/2004 |
| WO | WO-075456 A2 | 9/2004 |
| WO | 2006/012797 A1 | 2/2006 |
| WO | 2006/078611 A1 | 4/2006 |
| WO | 2006044847 A2 | 4/2006 |
| WO | 2006/078611 A2 | 7/2006 |
| WO | 2007/041295 A2 | 4/2007 |
| WO | WO-041295 A1 | 4/2007 |
| WO | 2007/041038 A1 | 6/2007 |
| WO | 2007/041038 A3 | 6/2007 |
| WO | 2008/100272 A2 | 8/2008 |
| WO | 2008/100272 A3 | 10/2008 |
| WO | 2009/117274 A2 | 9/2009 |
| WO | 2009/128997 A1 | 10/2009 |

(56) References Cited

FOREIGN PATENT DOCUMENTS

| WO | 2009/145958 A2 | 12/2009 |
|---|---|---|
| WO | 2010/006205 A1 | 1/2010 |
| WO | 2010/006211 A1 | 1/2010 |
| WO | WO-033666 A1 | 3/2010 |
| WO | 2010/047881 A1 | 4/2010 |
| WO | 2010/062798 A1 | 6/2010 |
| WO | 2010/065257 A1 | 6/2010 |
| WO | WO-120407 A1 | 10/2010 |
| WO | WO-028589 A2 | 3/2011 |
| WO | 2011/028589 A3 | 4/2011 |
| WO | 2011/097132 A2 | 8/2011 |
| WO | WO-097130 A2 | 8/2011 |
| WO | WO-109336 A2 | 9/2011 |
| WO | 2011/097132 A3 | 12/2011 |
| WO | 2011/149902 A2 | 12/2011 |
| WO | 2004/008738 A1 | 1/2024 |

OTHER PUBLICATIONS

Ando, et al., "A Multimedia Self-service Terminal with Conferencing Functions", IEEE, Jul. 5-7, 1995, pp. 357-362.
Android Amusement Corp., "What Marketing Secret . . . Renting Robots from Android Amusement Corp!", (Advertisement), 1982.
Applebome, "Planning Domesticated Robots for Tomorrow's Household", New York Times, http://www.theoldrobots.com/images17/dc17.JPG, Mar. 4, 1982, pp. 21, 23.
Baltus, et al., "Towards Personal Service Robots for the Elderly, Proceedings for the Elderly Workshop on Interactive Robots and Entertainment", Computer Science and Robotics, 2000.
Bar-Cohen, et al., "Virtual reality robotic telesurgery simulations using MEMICA haptic system", Internet, Mar. 5, 2001, pp. 1-7.
Bartholomew, "An Apothecary's Pharmacy", http://classes.bnf.fr/ema/grands/034.htm, pp. 1230-1240.
Bauer, Jeffrey C. et al., "Service Robots in Health Care: The Evolution of Mechanical Solutions to Human Resource Problems", Jun. 2003.
Bauer, John et al., "Remote telesurgical mentoring: feasibility and efficacy", IEEE, 2000, pp. 1-9.
Bischoff, "Design Concept and Realization of the Humanoid Service Robot HERMES", Field and Service Robotics, Springer, London, 1998, pp. 485-492.
Blackwell, Gerry, "Video: A Wireless LAN Killer App?", Internet, Apr. 16, 2002, pp. 1-3.
Breslow, Michael J. et al., "Effect of a multiple-site intensive care unit telemedicine program on clinical and economic outcome an alternative paradigm for intensivist staffing", Critical Care Med; vol. 32 No. 1, Jan. 2004, pp. 31-38.
Brooks, Rodney, "Remote Presence", Abstracts from Flesh & Machines, How Robots Will Change US, Feb. 2002, pp. 131-147.
Candelas, Herias et al., "Flexible virtual and remote laboratory for teaching Robotics", FORMATEX 2006; Proc. Advance in Control Education Madrid, Spain, Jun. 2006, pp. 21-23.
Celi, et al., "The EICU: It's not just telemedicine", Critical Care Medicine vol. 29, No. 8 (Supplement), Aug. 2001.
Cheetham, Anastasia et al., "Interface Development for a Child's Video Conferencing Robot", 2000, pp. 1-4.
Cleary, et al., "State of the art in surgical robotics: Clinical applications and technology challenges", Internet, Feb. 24, 2002, pp. 1-26.
CNN, "Floating 'droids' to roam space corridors of the future", Internet, Jan. 12, 2000, pp. 1-4.
cnn.com/technology, "Paging R.Robot: Machine helps doctors with patients", Internet, Sep. 30, 2003, 1-3.
Crowley, Susan L., "Hello to Our Future", AARP Bulletin, http://www.cs.cmu.ed/-nursebot/web/press/aarp 99_14/millennium.html, Jan. 2000.
Dalton, "Techniques for Web Telerobotics", PhD Thesis, University of Western Australia, http://telerobot.mech.uwa.edu.au/information.html, http://catalogue.library.uwa.edu.au/search, 2001, 27-62 pp. 149-191.

Davies, "Robotics in Minimally Invasive Surgery", Internet, 1995, pp. 5/1-5/2.
Digiorgio, James, "Is Your Emergency Department of the 'Leading Edge?'", Internet, 2005, pp. 1-4.
Discovery Channel Canada, "Inventing the Future: 2000 Years of Discovery", (Video Transcript), Jan. 2, 2000.
Elhajj, et al., "Supermedia in Internet-based telerobotic operations", Internet, 2001, pp. 1-14.
Elhajj, et al., "Synchronization and Control of Supermedia Transmission via the Internet", Proceedings of 2001 International Symposium on Intelligent Multimedia Video and Speech Processing., Hong Kong, May 2-4, 2001.
Ellison, et al., "Telerounding and Patient Satisfaction Following Surgery", pp. 523-530.
Fels, "Developing a Video-Mediated Communication System for Hospitalized Children", Telemedicine Journal, vol. 5, vol. 5, No. 2, 1999.
Fetterman, "Videoconferencing over the Internet", Internet, 2001, pp. 1-8.
Ghiasi, et al., "A Generic Web-based Teleoperations Architecture: Details and Experience", SPIE Conference on Telemanipulator and Telepresence Technologies VI, Sep. 1999.
Goldberg, et al., "Collaborative Teleoperation via the Internet", IEEE International Conference on Robotics and Automation, San Francisco, California, Apr. 2000.
Goldberg, "Desktop Teleoperation via the World Wide Web, Proceedings of the IEEE International Conference on Robotics and Automation", htto://citeseer.ist.osu.edu/cache/oaoers/cs/5/fto:zSzzSzusc.eduzSzoubzSziriszSzraiders.odf/aol, 1995, pp. 654-659.
Goldberg, "More Online Robots, Robots that Manipulate", Internet, Updated Aug. 2001, http://ford.ieor.berkeley.edu/ir/robots_a2.html, Aug. 2001.
Goldenberg, et al., "Telemedicine in Otolaryngology", American Journal of Otolaryngology vol. 23, No. 1, 2002, pp. 35-43.
Goldman, Lea, "Machine Dreams", Entrepreneurs, Forbes, May 27, 2002.
Gump, Michael D., "Robot Technology Improves VA Pharmacies", Internet, 2001, pp. 1-3.
Hameed, Mohammed et al., "A Review of Telemedicine", Journal of Telemedicine and Telecare., vol. 5, Supplement 1, 1999, pp. S1:103-S1:106.
Han, et al., "Construction of an Omnidirectional Mobile Robot Platform Based on Active Dual-Wheel Caster Mechanisms and Development of a Control Simulator", Kluwer Acedemic Publishers, vol. 29, Nov. 2000, pp. 257-275.
Handley, et al., "RFC 2327—SDP:Session Description Protocol", http://www.faqs.org/rfcs/rfc2327.html, Apr. 1998.
Hanebeck, et al., "ROMAN: A mobile Robotic Assistant for Indoor Service Applications", Proceedings of the 1997 IEEE/RSJ International Conference on Intelligent Robots and Systems, 1997.
Harmo, et al., "Moving Eye—Interactive Telepresence Over Internet With a Ball Shaped Mobile Robot", 2000.
Haule, et al., "Control Scheme for Delayed Teleoperation Tasks", Proceedings of the Pacific Rim Conference on Communications, Computer and Signal Processing, May 17, 1995.
Hees, William P., "Communications Design for a Remote Presence Robot", Jan. 14, 2002.
Holmberg, "Development of a Holonomic Mobile Robot for Mobile Manipulation Tasks", International Conference on Field and Service Robotics, Pittsburgh, PA, Aug. 1999.
Int'l Communication Union, "ITU-T H.323 Packet-based multimedia communications", http://www.itu.int/rec/T-REC-H.323-199802-S/en, Feb. 1998.
Ishiguro, "Integrating a Perceptual Information Infrastructure with Robotic Avatars: A Framework for Tele-Existence", Proceeding of IEEE Conference on Intelligent Robots and Systems, 1999, pp. 1032-1038.
Ishihara, et al., "Intelligent Microrobot DDS (Drug Delivery System) Measured and Controlled by Ultrasonics", IEEE/RSJ, vol. 2, Nov. 3-5, 1991, pp. 1145-115.
Ivanova, Natali, "Master's thesis: Internet Based Interface for Control of a Mobile Robot", Department of Numerical Analysis and Computer Science, 2003, 59 pages.

(56) References Cited

OTHER PUBLICATIONS

Jenkins, et al., "Telehealth Advancing Nursing Practice", Nursing Outlook, vol. 49, No. 2, Mar./Apr. 2001.
Johanson, "Supporting video-mediated communication over the Internet", Chalmers University of Technology, Dept of Computer Engineering, Gothenburg, Sweden, 2003.
Jouppi, et al., "Mutually-Immersive Audio Telepresence", Audio Engineering Society Convention Paper presented at 113th Convention, Oct. 2002.
Jouppi, Norman et al., "First Steps Towards Mutually-Immersive Mobile Telepresence", CSCW, 02, New Orleans LA, Nov. 16-20, 2002.
Kanehiro, Fumio et al., "Virtual Humanoid Robot Platform to Develop Controllers of Real Humanoid Robots without Porting", IEEE, 2001, pp. 3217-3276.
Kaplan, A. E. et al., "An Internet Accessible Telepresence", {aek keshav nls jhv}@research.att.com, AT&T Bell Laboratories, Murray Hill, N.J., pp. 1-7.
Keller, et al., "Raven Interface Project", http://upclose.lrdc.pitt.edu/people/louw_assets/Raven_Slides.pps, Fall 2001.
Khatib, "Robots in Human Environments", Proc. International Conference on Control, Automation, Robotics, and Vision ICRACV2000, Singapore, Dec. 2000, pp. 454-457.
Kuzuoka, et al., "Can The GestureCam Be A Surrogate?", Proceedings of the Fourth European Conference on Computer- Supported Cooperative Work, September 10-14, pp. 181-196.
Lane, "Automated Aides", Newsday, http://www.cs.cum.edu/nursebot/web/press/nd4380.htm, Oct. 17, 2000.
Lee, et al., "A novel method of surgical instruction: International telementoring", Internet, 1998, pp. 1-4.
Lim, Hun-Ok et al., "Control to Realize Human-like Walking of a Biped Humanoid Robot", IEEE, 2000, pp. 3271-3276.
Linebarger, John M et al., "Concurrency Control Mechanisms for Closely Coupled Collaboration in Multithreaded Virtual Environments", Presence, Special Issue on Advances in Collaborative VEs, 2004.
Loeb, et al., "Virtual Visit: Improving Communication for Those Who Need It Most", Stud Health Technol Inform .; 94: 2003 pp. 302-308.
Long, "HelpMate Robotics, Inc. (Formerly Transitions Research Corporation) Robot Navigation Technology", NIST Special Publication, http://www.atp.nist.gov/eao/sp950-1/helpmate.htm, Mar. 1999, pp. 950-951.
Luna, Nancy, "Robot a new face on geriatric care", OC Register, Aug. 6, 2003.
Mack, "Minimally invasive and robotic surgery", Internet IEEE, 2001, pp. 568-572.
Mair, "Telepresence - The Technology. And Its Economic and Social Implications", IEEE Technology and Society, 1997.
Martin, Anya , "Days Ahead", Assisted Living Today, vol. 9, November/Dec. 2002, pp. 19-22.
Mccardle, et al., "The challenge of utilizing new technology in design education", Internet, 2000, pp. 122-127.
Meng, et al., "E-Service Robot in Home Healthcare", Proceedings of the 2000 IEEE/RSJ, International Conference on Intelligent Robots and Systems, 2000, pp. 832-837.
Michaud, "Introducing Nursebot", The Boston Globe, http://www.cs.cmu.edu/nursebot/web/press/globe 3 01/index.html, Sep. 11, 2001, pp. 1-5.
Montemerlo, "Telepresence: Experiments in Next Generation Internet", CMU Robotics Institute, http://www.ri.cmu.edu/creative/archives.htm (Video/Transcript), Oct. 20, 1998.
Murphy, "Introduction to A1 Robotics", A Bradford Book, 2000, p. 487.
Nakajima, et al., "A Multimedia Teleteaching System using an Electronic Whiteboard for Two Way Communication of Motion Videos and Chalkboards", IEEE, 1993, pp. 436-441.
Nomadic Technologies Inc., "Nomad XR4000 Hardware Manual", Release 1.0, Mar. 1999.
Nt'l Energy Res Sci Comp Ctr, "Berkeley Lab's RAGE Telepresence Robot Captures R&D100 Award", http://www.nersc.gov/news/newsroom/RAGE070202.php, Jul. 2, 2002,.
Ogata, et al., "Development of Emotional Communication Robot: WAMOEBA-2r- Experimental evaluation .", IEEE, 2000, pp. 175-180.
Ogata, et al., "Emotional Communication Robot: WAMOEBA-2R - Emotion Model and Evaluation Experiments", Internet, 1999, pp. 1-16.
Oh, et al., "Autonomous Battery Recharging for Indoor Mobile Robots", Proceedings of Australian Conference on Robotics and Automation, http://users.rsise.anu.edu.au/rsl/rsl_papers/ACRA2000/Auto_Recharge Paper. pdf, 2000.
Ojha, A. K., "An application of Virtual Reality in Rehabilitation", IEEE, Apr. 10-13, 1994, pp. 4-6.
Paulos, et al., "A World Wide Web Telerobotic Remote Environment Browser", http://vive.cs.berkeley.edu/capek, 1995.
Paulos, "Designing Personal Tele-embodiment", IEEE International Conference on Robotics and Automation http://www.prop.org/papers/icra98.pdf, 1998.
Paulos, "Prop: Personal Roving Presence", Acm: Chi Proceedings of CHI '98, http://www.prop.org/papers/chi98.pdf, 1998, p. 6.
Paulos, et al., "Ubiquitous Tele-embodiment: Applications and Implications", International Journal of Human Computer Studies, vol. 46, No. 6, Jun. 1997, pp. 861-877.
Paulos, "Video of PROP 2 at Richmond Field Station", www.prop.org Printout of Home Page of Website and two-page Transcript of the audio portion of said PROP Video, May 2001.
Paulos, Eric J., "Personal Tele-Embodiment", UC Berkeley, Fall 2001.
Pin, et al., "A New Family of Omnidirectional and Holonomic Wheeled Platforms for Mobile Robots", IEEE, vol. 10, No. 4, Aug. 1994.
Rovetta, et al., "A New Telerobotic Application: Remote Laparoscopic Surgery Using Satellites and and optical fiber Networks for Data Exchange", International Journal of Robotics Research, Jun. 1, 1996, pp. 267-279.
Roy, et al., "Towards Personal Service Robots for the Elderly", Internet, Mar. 7, 2002, 7 pgs.
Salemi, et al., "MILO: Personal robot platform", Internet, 2005, pp. 1-6.
Sandt, Frederic et al., "Perceptions for a Transport Robot in Public Environments", IROS, 1997.
Schaeffer, "Care-O-bot: A System for Assisting Elderly or Disabled Persons in Home Environments", Proceedings of AAATE-99, http://morpha.de/download/publications/IPA, 1999,.
Schulz, "Web Interfaces for Mobile Robots in Public Places", Robotics & Automation Magazine, IEEE, vol. 7, Issue 1, Mar. 2000.
Shimoga, et al., "Touch and force reflection for telepresence surgery", IEEE, 1994, pp. 1049-1050.
Siegwart, "Interacting Mobile Robots on the Web", Proceedings of the 1999 IEEE International Conference on Robotics and Automation, May 1999.
Simmons, "Xavier: An Autonomous Mobile Robot on the Web", IEEE Robotics and Automation Magazine, 1999, pp. 43-48.
Spawar Systems Center, "Robart", San Diego, CA, http://www.nosc.mil/robots/land/robart/robart.html, 1998, pp. 1-8.
Stephenson, Gary, "Dr. Robot Tested at Hopkins", Internet, Aug. 5, 2003, pp. 1-2.
Stoianovici, et al., "Robotic Tools for Minimally Invasive Urologic Surgery", Internet, Dec. 2002, pp. 1-17.
Suplee, , "Mastering the Robot", The Washington Post, http://www.cs.cmu.edu-nursebotlweb/press/wash/index.html, Sep. 17, 2000, p. A01.
Tahboub, Karim A et al., "Dynamics Analysis and Control of a Holonomic Vehicle With Continously Variable Transmission", Journal of Dynamic Systems, Measurement and Control ASME vol. 124, Mar. 2002, pp. 118-126.
Tendick, et al., "Human-Machine Interfaces for Minimally Invasive Surgery", IEEE, 1997, pp. 2771-2776.
Thrun, et al., "Probabilistic Algorithms and the Interactive Museum Tour-Guide Robot Minerva", Internet, 2000, pp. 1-35.

(56) References Cited

OTHER PUBLICATIONS

Tzafestas, et al., "VR-based Teleoperation of a Mobile Robotic Assistant: Progress Report", Internet, Nov. 2000, pp. 1-23.
Urquhart, Kim, "InTouch's robotic Companion 'beams up' healthcare experts", Medical Device Daily, vol. 7, No. 39, Feb. 27, 2003, p. 1,4.
Weiss, et al., "Telework and video-mediated communication: Importance of real-time, interactive communication for workers with disabilities", California State University Northridge http://www.csun.edu/cod/conf/1999/proceedings/session0238.html, pp. 1-4.
West, et al., "Design of Ball Wheel Mechanisms for Omnidirectional Vehicles with Full Mobility and Invariant Kinematics", Journal of Mechanical Design, vol. 119, Jun. 1997, pp. 153-161.
Yamasaki, et al., "Applying Personal Robots and Active Interface to Video Conference Systems", Internet, 1995, pp. 243-248.
Yamauchi, "PackBot: A Versatile Platform for Military Robotics", Internet, 2004, pp. 1-10.
Yong, et al., "Robot task execution with telepresence using virtual reality technology", Internet, 1998, pp. 1-8.
Zamrazil, Kristie, "Telemedicine in Texas: Public Policy Concerns", House Research Organization Focus Report, Texas House of Representatives, http://www.hro.house.state.tx.US/focus/telemed.pdf, May 5, 2000, pp. 76-22.
Zipperer, Lorri, "Robotic dispensing system", 1999, pp. 1-2.
Zorn, Benjamin G., "Ubiquitous Telepresence", http://www.cs.colorado.edu/-zorn/utlvision/vision.html, May 5, 1996.
Theodosiou et al., "MuLVAT: A Video Annotation Tool Based on XML-Dictionaries and Shot Clustering", 19th International Conference, Artificial Neural Networks-ICANN, Sep. 14-17, 2009, pp. 913-922.
Time, Lists, "Office Coworker Robot", Best Inventions of 2001, available online at <http://content.time.com/time/specials/packages/article/0,28804,1936165_1936255_1936640,00.html>, Nov. 19, 2001, 2 pages.
Tipsuwan et al., "Gain Adaptation of Networked Mobile Robot to Compensate QoS Deterioration", vol. 4, 28th Annual Conference of the Industrial Electronics Society, Nov. 5-8, 2002, pp. 3146-3151.
Tsui et al., "Exploring Use Cases for Telepresence Robots", 6th ACM/IEEE International Conference on Human- Robot Interaction (HRI), Mar. 2011, 7 pages.
Tyrrell et al., "Teleconsultation in Psychology: The Use of Videolinks for Interviewing and Assessing Elderly Patients", British Geriatrics Society, Age and Ageing, vol. 30, No. 3, May 2001, pp. 191-195.
Umass Lowell Robotics Lab, "Robotics Lab @ UMASS Lowell", Department of Computer Science, Brochure, 2011, 2 pages.
Video Middleware Cookbook, "H.350 Directory Services for Multimedia", 4 pages.
Weaver et al., "Monitoring and Controling Using the Internet and Java", Proceedings of the 25th Annual Conference of the IEEE Industrial Electronics Society, vol. 3, 1999, pp. 1152-1158.
Appeal from the U.S. District Court for the Central District of California in case No. 11-cv-9185, Judge Percy Anderson, Joint Appendix, vol. I of IV, Jun. 24, 2013, pp. A1-A6357.
Appeal from the U.S. District Court for the Central District of California in case No. 11-cv-9185, Judge Percy Anderson, Joint Appendix, vol. II of IV, Jun. 24, 2013, pp. A6849-A10634.
Appeal from the U.S. District Court for the Central District of California in case No. 11-cv-9185, Judge Percy Anderson, Joint Appendix, vol. III of IV, Jun. 24, 2013, pp. A10654-A15517.
Appeal from the U.S. District Court for the Central District of California in case No. 11-cv-9185, Judge Percy Anderson, Joint Appendix, vol. IV of IV, Jun. 24, 2013, pp. A15677-A18127.
Reply Brief for Defendant-Appellee VGO Communications, Inc., Appeal from the U.S. District Court for the Central District of California, in Case No. 2:11-cv-9185, Judge Percy Anderson, May 28, 2013, 75 pages.
Civil Minutes-General: Case No. Cv 11-9185PA (AJWx), InTouch Tech., Inc. v. VGo Commons, Inc., U.S. District Court for the Central District of California, Judge Percy Anderson, Sep. 10, 2012, 7 pages.

"Defendant VGo Communications, Inc.'s Invalidity Contentions Pursuant to the Feb. 27, 2012 Civil Minute Order", U.S. District Court for the Central District of California, in Case No. CV11-9185 Pa, May 2, 2012, 143 pages.
Defendant-Counterclaimant VGo Communications, Inc.'s Supplemental Invalidity Contentions Pursuant to the Feb. 27, 2012 Civil Minute Order, U.S. District Court for the Central District of California, Case No. CV11-9185 Pa, May 14, 2012, 228 pages.
"Magne Charge", Smart Power for Electric Vehicles, General Motors Corporation, U.S. Appl. No. 75/189,637, Registration No. 2114006, Filing Date: Oct. 29, 1996, Aug. 26, 1997, 2 pages.
Opening Brief for Plaintiff-Appellant InTouch Technologies, Inc., Appeal from the U.S. District Court for the Central District of California in Case No. 11-cv-9185, Judge Percy Anderson, Apr. 12, 2013, 187 pages.
Reply Brief for Plaintiff-Appellant InTouch Technologies, Inc., Appeal from the U.S. District Court for the Central District of California in Case No. 11-cv-9185, Judge Percy Anderson, Jun. 14, 2013, 39 pages.
"Using your Infrared Cell Phone Camera", available online on <http://www.catsdomain.com/xray/about.htm>, retrieved on Jan. 23, 2014, Courtesy of Internet Wayback Machine, Jan. 30, 2010, 4 pages.
Office Action received for Chinese Patent Application No. 200680044698.0 on Nov. 4, 2010. (9 pages of Official Copy and 17 pages of English Translation).
Active Media, Inc., "Saphira Software Manual", Real World, Saphira Version 5.3, 1997, 105 pages.
Activmedia Robotics Llc, "Pioneer 2/PeopleBot™", Operations Manual, Version 9, Oct. 2001, 78 pages.
Adams, Chris, "Simulation of Adaptive Behavior (SAB'02) - From Animals to Animats 7", Mobile Robotics Research Group, The Seventh International Conference, available online at: < http://www.dai.ed.ac.uk/groups/mrg/MRG.html>, retrieved on Jan. 22, 2014, Aug. 4-11, 2002, 1 page.
Apple Inc., "I Phone", iPhone Series, XP002696350, Sep. 21, 2012, pp. 1-29.
Barrett, Rick, "Video Conferencing Business Soars as Companies Cut Travel; Some Travel Cuts are Permanent", available online at <http://www.ivci.com/international_videoconferencing_news_videoconferencing_news_19.html>, May 13, 2002, 2 pages.
Blaer et al., "TopBot: Automated Network Topology Detection With a Mobile Robot", IEEE, Proceedings of the 2003 International Conference on Robotics and Automation, Taipei, Taiwan, Sep. 14-19, 2003, pp. 1582-1587.
Bradner, S., "The Internet Standards Process -- Revision 3", Network Working Group, Request for Comments: 2026, BCP: 9, Obsoletes: 1602, Category: Best Current Practice, Oct. 1996, pp. 1-36.
Brooks, Rodney A., "A Robust Layered Control System for a Mobile Robot", IEEE, Journal of Robotics and Automation, vol. 2, No. 1, Mar. 1986, pp. 14-23.
Christensen et al., "BeeSoft User's Guide and Reference", Robots for the Real World™, Real World Interface, Inc., Sep. 26, 1997, 203 pages.
Chu et al., "Detection of Target Mobile Signal Strength", Technical Development, Motorola Inc., Jan. 1999, pp. 205-206.
Dario et al., "A Robot Workstation for Diagnosis and Physical Therapy", IEEE Catalog No. 88TH0234-5, Centro "E. Piaggio" University of Pisa, Italy, 1989, pp. 67-72.
Davis, Erik, "Telefriend, Meet iRobot, The Smartest Webcam on Wheels", Wired Magazine, Issue 8.09, available online at <http://www.wired.com/wired/archive/8.09/irobot.html?pg=1&topic=&topic_set=>, retrieved on Jul. 7, 2012, Sep. 2000, 3 pages.
Dean et al., "1992 AAAI Robot Exhibition and Competition", Articles, Al Magazine, vol. 14, No. 1, 1993, 15 pages.
Dudenhoeffer et al., "Command and Control Architectures for Autonomous Micro- Robotic Forces", FY00 Project Report, Idaho National Engineering and Environmental Laboratory, Human Systems Engineering and Sciences Department, Idaho Falls, Apr. 2001, 43 pages.

(56) References Cited

OTHER PUBLICATIONS

Elhajj et al., "Real-Time Haptic Feedback in Internet-Based Telerobotic Operation", IEEE International Conference on Electro/Information Technology, Jun. 2000, 10 pages.

Evans et al., "HelpMate: The Trackless Robotic Courier", PYXIS, available online at <http://www.pyxis.com/>, 3 pages.

Fiorini et al., "Health Care Robotics: A Progress Report", IEEE International Conference on Robotics and Automation, vol. 2, Apr. 20-25, 1997, pp. 1271-1276.

Fong, Terrence, "Collaborative Control: A Robot-Centric Model for Vehicle Teleoperation", The Robotics Institute Carnegie Mellon University, Nov. 2001, 197 pages.

Gaidioz et al., "Synchronizing Network Probes to Avoid Measurement Intrusiveness with the Network Weather Service", High-Performance Distributed Computing, Proceedings of the Ninth International Symposium, 2000, pp. 147-154.

Garner et al., "The Application of Telepresence in Medicine", BT Technology Journal, vol. 15, No. 4, Oct. 1, 1997, pp. 181-187.

GOSTAI "Gostai Jazz: Robotic Telepresence", available online at <http://www.gostai.com>, 4 pages.

Itu, "A Far End Camera Control Protocol for Videoconferences Using H.224", Transmission of Non-Telephone Signals, ITU-T, Telecommunication Standardization Sector of Itu, H.281, Nov. 1994, 12 pages.

Jacobs et al., "Applying Telemedicine to Outpatient Physical Therapy", AMIA, Annual Symposium Proceedings, 2002, 1 page.

Kurlowicz et al., "The Mini Mental State Examination (MMSE)", The Hartford Institute for Geriatric Nursing, Journal of Psychiatric Research, No. 3, Jan. 1999, 2 pages.

Leifer et al., "Viprr: A Virtually In Person Rehabilitation Robot", Proceedings of 1997 International Conference on Rehabilitation Robotics, Apr. 14-15, 1997, 4 pages.

Lemaire, Edward, "Using Communication Technology to Enhance Rehabilitation Services", Terry Fox Mobile Clinic, The Rehabilitation Centre, Ottawa, Canada, Version 2.0, 1998 - 2001, 104 pages.

Minsky, Marvin, "Telepresence", OMNI Magazine, Jun. 1980, 6 pages.

Nakazato et al., "Group-Based Interface for Content-Based Image Retrieval", Proceedings of the Working Conference on Advanced Visual Interfaces, 2002, pp. 187-194.

Nakazato et al., "Group-Oriented User Interface for Digital Image Management", Journal of Visual Languages and Computing, vol. 14, No. 4, Aug. 2003, pp. 45-46.

Noritsugu et al., "Application of Rubber Artificial Muscle Manipulator as a Rehabilitation Robot", Mechatronics, IEEE/ASME Transactions, vol. 2, No. 4, Dec. 1997, pp. 259-267.

North, Michael, "Telemedicine: Sample Script and Specifications for a Demonstration of Simple Medical Diagnosis and Treatment Using Live Two-Way Video on a Computer Network", Greenstar Corporation, 1998, 5 pages.

Osborn et al., "Quality of Life Technology Center", QoLT Research Overview: A National Science Foundation Engineering Research Center, Carnegie Mellon University of Pittsburgh, 2 pages.

Piquepaille, Roland, "How New Technologies are Modifying Our Way of Life", Roland Piquepaille's Technology Trends, This Blog and its RSS Feed Are Moving, Oct. 31, 2004, 2 pages.

Radvision, "Making Sense of Bandwidth the NetSense Way", Network Congestion in Unmanaged Networks Bandwidth Estimation and Adaptation Techniques, Radvision's Netsense Technology, 2010, 7 pages.

Reynolds et al., "Review of Robotic Telemedicine Utilization in Intensive Care Units (ICUs)", 11th Annual ATA Symposium, Tampa, Florida, 2011, 1 page.

Roy et al., "Towards Personal Service Robots for the Elderly", Workshop on Interactive Robots and Entertainment (WIRE 2000), vol. 25, Apr. 30 - May 1, 2000, 7 pages.

Telepresence Research, Inc., "Telepresence Mobile Robot System", available online at <http://www.telepresence.com/telepresence-research/TELEROBOT/>, retrieved on Nov. 23, 2010, Feb. 20, 1995, 3 pages.

Screenshot Showing Google Date for Lemaire Telehealth Manual, Screenshot Retrieved on Dec. 18, 2014, 1 page.

Nomadic Technologies, Inc., "Nomad Scout Language Reference Manual", Software Version: 2.7, Part No. DOC00002, Jul. 12, 1999, 47 pages.

"Appeal from the U.S. District Court for the Central District of California in No. 11-CV-9185, Judge Percy Anderson", May 9, 2014, pp. 1-48.

"Google Translation of: Innovations Report", From Research Project to Television Star: Care-O-bot in ZDF Series, available at <http://www.innovations-report.de/specials/printa.php?id=5157>, Sep. 28, 2001, 2 pages.

"MPEG File Format Summary", available at <http://www.fileformat.info/format/mpeg/egff.htm>, retrieved on Jun. 25, 2014, Feb. 1, 2001, 7 pages.

Koenen, Rob, "MPEG-4: A Powerful Standard for Use in Web and Television Environments", (KPN Research), available at <http://www.w3.org/Architecture/1998/06/Workshop/paper26>, Jul. 1, 1998, 4 pages.

Nomadic Technologies, Inc., "Nomad Scout User's Manual", Software Version 2.7, Part No. DOC00004, Jul. 12, 1999, pp. 1-59.

Acm Digital Library Record, Autonomous Robots, vol. 11, No. 1, Table of Content, available at <http://dl.acm.org/citation.cfm?id=591550&picked=prox&cfid=360891374&cftoken=35225929>, Jul. 2001, 2 pages.

Brenner, Pablo, "A Technical Tutorial on the IEEE 802.11 Protocol", BreezeCOM Wireless Communications, Jul. 18, 1996, pp. 1-24.

Cmu Course, "16x62 Robot User's Manual", (Describing the Nomad Scout), Carnegie Mellon University, Feb. 1, 2001, 11 pages.

Library of Congress, "008-Fixed-Length Data Elements (Nr)", Mar. 21 Format for Classification Data, available at <http://www.loc.gov/marc/classification/cd008.html>, retrieved on Jul. 22, 2014, pp. 1-14.

Panusopone et al., "Performance Comparison of MPEG-4 and H.263+ for Streaming Video Applications", Circuits Systems Signal Processing, vol. 20, No. 3, 2001, pp. 293-309.

Paulos et al., "Personal Tele-Embodiment", Chapter 9 in Goldberg et al., Ed., "Beyond Webcams", MIT Press, Jan. 4, 2002, pp. 155-167.

Paulos et al., "Social Tele-Embodiment: Understanding Presence", Autonomous Robots, vol. 11, No. 1, Kluwer Academic Publishers, Jul. 2001, pp. 87-95.

Paulos, Eric John, "Personal Tele-Embodiment", Introductory and Cover Pages from 2001 Dissertation Including Contents table, together with E-mails Relating thereto from UC Berkeley Libraries, as Shelved at UC Berkeley Engineering Library (Northern Regional Library Facility), May 8, 2002, 25 pages (including 4 pages of e-mails).

Paulos, Eric John, "Personal Tele-Embodiment", OskiCat Catalog Record, UCB Library Catalog, Results page and MARC Display, retrieved on Jun. 14, 2014, 3 pages.

Schraft et al., "Care-O-bot™: The Concept of a System for Assisting Elderly or Disabled Persons in Home Enviornments", IEEE Proceedings of the 24th Annual Conference of the Industrial Electronics Society, IECON '98, August 31-Sep. 4, 1998, pp. 2476-2481.

Fulbright et al., "SWAMI: An Autonomous Mobile Robot for Inspection of Nuclear Waste of Storage Facilities", Autonomous Robots, vol. 2, 1995, pp. 225-235.

Barrett, "Video Conferencing Business Soars as Companies Cut Travel; Some Travel Cuts Are Permanent", http://www.ivci.com/international_videoconferencing_news_videoconferencing_news_19.html, Mar. 13, 2002.

Brooks, "A Robust Layered Control System for a Mobile Robot," IEEE Journal of Robotics and Automation, 2 (1), Mar. 1986, 10 pgs.

Davis, "Meet iRobot, The Smartest Webcam on Wheels," Wired Magazine, 8.09, http://www.wired.com/wired/archive/8.09/irobot_pr.html, Sep. 2000, 2 pgs.

Dean, et al., "1992 AAAI Robot Exhibition and Competition," AI Magazine, Spring 1993, 10 pgs.

"Defendant VGo Communications, Inc.'s Invalidity Contentions Pursuant to the Feb. 27, 2012 Civil Minute Order", May 2, 2012.

(56) References Cited

OTHER PUBLICATIONS

"Defendant-Counterclaimant VGo Communications, Inc.'s Supplemental Invalidity Contentions Pursuant to the Feb. 27, 2012 Civil Minute Order", May 14, 2012.
Dudenhoeffer, et al., "Command And Control Architectures for Autonomous Micro-Robotic Forces", http://www.inl.gov/technicalpublications/Documents/3157051.pdf, Apr. 2001.
Elhajj, "Real-Time Haptic Feedback in Internet-Based Telerobotic Operation", IEEE International Conference on Electro/Information Technology, http://www.egr.msu.edu/~ralab-web/cgi_bin/internet-teleoperation.php, Jun. 2000.
Fiorini, et al., "Health Care Robotics: A Progress Report", IEEE International Conference on Robotics and Automation, 1997., Apr. 1997, pp. 1271-1276.
Fong, "Collaborative Control: A Robot-Centric Model for Vehicle Teleoperation", The Robotics Institute Carnegie Mellon University, http://web.archive.org/web/20030504040803/www.ricmu.edu/cgi-bin/tech_reports.cgi?year=2001&text=0, Nov. 2001.
Grow, "Office Coworker Robot," Time Magazine, http://www.time.com/time/specials/packages/article/0,28804, 1936165_1936255_1936640,00.html, Nov. 19, 2001, 2 pgs.
ITU, "ITU-T H.281 A Far End Camera Control Protocol for Videoconferences using H.224", http://www.itu.int/rec/T-RECH.281-199411-I/en, Nov. 1994.
ITU, "ITU-T H.450.11 Call Intrusion Supplementary Service for H.323", http://www.itu.int/rec/T-RECH.450.11-200103-I/en, Mar. 2001.
ITU, "ITU-T H.450.9 Call Completion Supplementary Services for H.323", http://www.itu.int/rec/T-RECH.450.9-200011-I/en, Nov. 2000.
Knight, et al., "Active Visual Alignment of a Mobile Stereo Camera Platform", Proceedings of the IEEE, International Conference on Robotics and Automation, San Francisco, Apr. 24-28, 2000, pp. 3202-3208.
Metz, "HP Labs", PCMAG.com, http://www.pcmag.com/article2/0,2817,1130820,00.asp, Jul. 1, 2003.
Picturetel, "PictureTel Live200 for Windows NT Product Guide", http://support.polycom.com/global/documents/support/user/products/video/live200_live200NT_product_guide.pdf, Nov. 1994.
"PictureTel Adds New Features and Functionality to Its Award-Winning Live200 Desktop Videoconferencing System", PR Newswire Association, LLC, Gale, Cengage Learning, http://www.thefreelibrary.com/PictureTel+Adds+New+Features+And+Functionality+To+Its+Award-Winning...-a019512804, Jun. 13, 1997.
Roach, "Automatic Call Back Service in SIP", http://tools.ietf.org/pdf/draftroach-sip-acb-00.pdf, Mar. 2000.
Summers, "Microsoft NetMeeting 3 Features excerpt from Official Microsoft NetMeeting 3.0 Book", http://technet.microsoft.com/en-us/library/cc723477.aspx#XSLTsection121121120120, excerpt from Microsoft Press http://www.computerbooksonline.com/abook.asp?i=0735605823, Mar. 1999.
U.S. Appl. No. 10/783,760, filed, Feb. 20, 2004, Wang, et al., 48 pgs.
U.S. Appl. No. 60/449,762, filed, Feb. 24, 2003, Wang, et al., 28 pgs.
Weiss, et al., "PEBBLES: A Personal Technology for Meeting Education, Social and Emotional Needs of Hospitalised Children", Personal and Ubiquitous Computing 5, Springer-Verlag London Ltd., 2001, pp. 157-168.
Zambroski, "CMU, Pitt Developing 'nursebot'", http://www.cs.cmu.edu/~nursebot/web/press/tribunereview.html, Oct. 27, 2000.

\* cited by examiner

TELEROBOTIC SYSTEM WITH A DUAL APPLICATION SCREEN PRESENTATION

BACKGROUND

1. Technical Field

The subject matter disclosed generally relates to the field of proctoring.

2. Related Art

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. One of the robotic arms in the Wang system moves an endoscope that has a camera. The camera allows a surgeon to view a surgical area of a patient.

There has been marketed a mobile robot by InTouch Technologies, Inc., the assignee of this application. The InTouch robot is controlled by a user at a remote station. The remote station may be a personal computer with a joystick that allows the user to remotely control the movement of the robot. Both the robot and remote station have cameras, monitors, speakers and microphones that allow two-way video/audio communication between the remote station operator and personnel of the robot site.

The InTouch system has been used to remotely assist and train medical personnel. For example, a medical specialist at one location can view the patient at a remote location and provide proctoring to medical personnel at the patient site. It would be desirable to enhance the proctoring capability of the InTouch system.

DETAILED DESCRIPTION

Disclosed is a proctoring system that includes a communication device coupled to a remote station. The remote station has a visual display that displays first information relating to an action that causes an effect on an object, and simultaneously displays second information relating to the effect on the object. The remote station includes at least one input device that allows a communication to be transmitted by an operator to the communication device. By way of example, during the deployment of a heart stent, a specialist doctor may remotely view real-time fluoroscopy imagery and patient hemodynamics. The specialist can remotely proctor medical personnel on the proper orientation and timing requirements for installing the stent. The fluoroscopy imagery displays an image of the stent being inserted into a beating heart. The stent will cause an effect on the heart such as a change in heart beat. The hemodynamics provide data regarding the beating heart, which is the effect of the stent. The simultaneous display of patient hemodynamics and fluoroscopy imagery provide the specialist with real-time data so that they can issue a command such as "deploy now" to insert the stent. Alternatively, the proctoring specialist would converse with the intra-operative surgeon to confer on the pattern of hemodynamic information being received and suggest through this information that "as we can observe this is the ideal timing of implant deployment".

Figure 1:
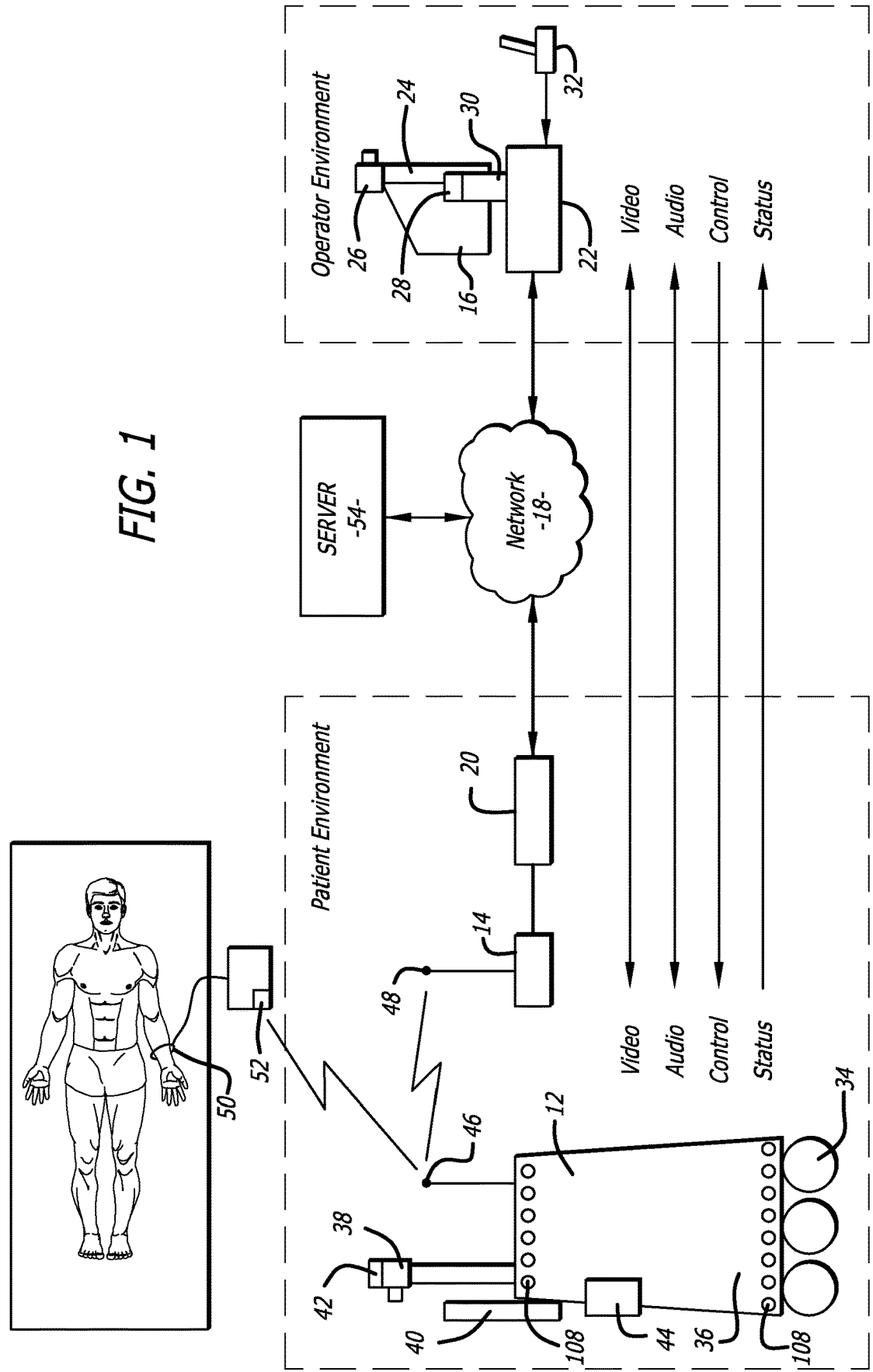
FIG. 1 is an illustration of a robotic system.

Referring to the drawings more particularly by reference numbers, FIG. 1 shows a system 10. The robotic system includes a robot 12, a base station 14 and a remote control station 16. The remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device. By way of example, the base station 14 may be a wireless router. Alternatively, the robot 12 may have a direct connection to the network thru for example a satellite.

The remote control station 16 may include a computer 22 that has a monitor 24, a camera 26, a microphone 28 and a speaker 30. The computer 22 may also contain an input device 32 such as a joystick or a mouse. The control station 16 is typically located in a place that is remote from the robot 12. Although only one remote control station 16 is shown, the system 10 may include a plurality of remote stations. In general any number of robots 12 may be controlled by any number of remote stations 16 or other robots 12. For example, one remote station 16 may be coupled to a plurality of robots 12, or one robot 12 may be coupled to a plurality of remote stations 16, or a plurality of robots 12.

Each robot 12 includes a movement platform 34 that is attached to a robot housing 36. Also attached to the robot housing 36 are a camera 38, a monitor 40, a microphone(s) 42 and a speaker(s) 44. The microphone 42 and speaker 30 may create a stereophonic sound. The robot 12 may also have an antenna 46 that is wirelessly coupled to an antenna 48 of the base station 14. The system 10 allows a user at the remote control station 16 to move the robot 12 through operation of the input device 32. The robot camera 38 is coupled to the remote monitor 24 so that a user at the remote station 16 can view a patient. Likewise, the robot monitor 40 is coupled to the remote camera 26 so that the patient may view the user. The microphones 28 and 42, and speakers 30 and 44, allow for audible communication between the patient and the user.

The remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

The robot 12 may be coupled to one or more medical monitoring devices 50. The medical monitoring device 50 can take medical data from a patient. By way of example, the medical monitoring device 50 may be a stethoscope, a pulse oximeter and/or an EKG monitor. The medical monitoring device 50 may contain a wireless transmitter 52 that transmits the patient data to the robot 12. The wirelessly transmitted data may be received by antennae 46, or a separate antennae (not shown). The robot 12 can then transmit the data to the remote station 16. The medical devices 50 may include a fluoroscope that can generate fluoroscopy images. Additionally, the medical devices may generate patient hemodynamic data such as heart rate.

The wireless transmission from the medical monitoring device 50 may be in accord with various wireless standards such as IEEE. The standard used to transmit data from the medical monitoring device 50 should not interfere with the wireless communication between the robot 12 and the base station 14. Although wireless transmission is shown and described, it is to be understood that the medical monitoring device 50 can be coupled to the robot 12 by wires (not shown).

When transmitting fluoroscopy imagery and patient hemodynamics, the system can combine hemodynamic data with a frame of the fluoroscopy imagery into a double-wide frame that is transmitted to the remote station for split screen display. The stitching of the two frames would occur prior to compression, enabling the compression algorithm (e.g. MPEG-4) to utilize redundant information that may occur between the two frames. This potentially will result in equivalent quality and lower bandwidth as compared to two streams compressed and transmitted separately. Alternatively, the fluoroscopy imagery and hemodynamics can be transmitted in a decoupled manner and then combined with timing information such as time stamps that are inserted into the information before transmission.

The remote station 16 may be coupled to a server 54 through the network 18. The server 54 may contain electronic medical records of a patient. By way of example, the electronic medical records may include written records of treatment, patient history, medication information, a medical image, such as an e-ray, MRI or CT scan, EKGs, laboratory results, physician notes, etc. The medical records can be retrieved from the server 54 and displayed by the monitor 24 of the remote station 16. In lieu of, or in addition to, the medical records can be stored in the mobile robot 12. The remote station 16 may allow the physician to modify the records and then store the modified records back in the server 54 and/or robot 12.

Figure 2:
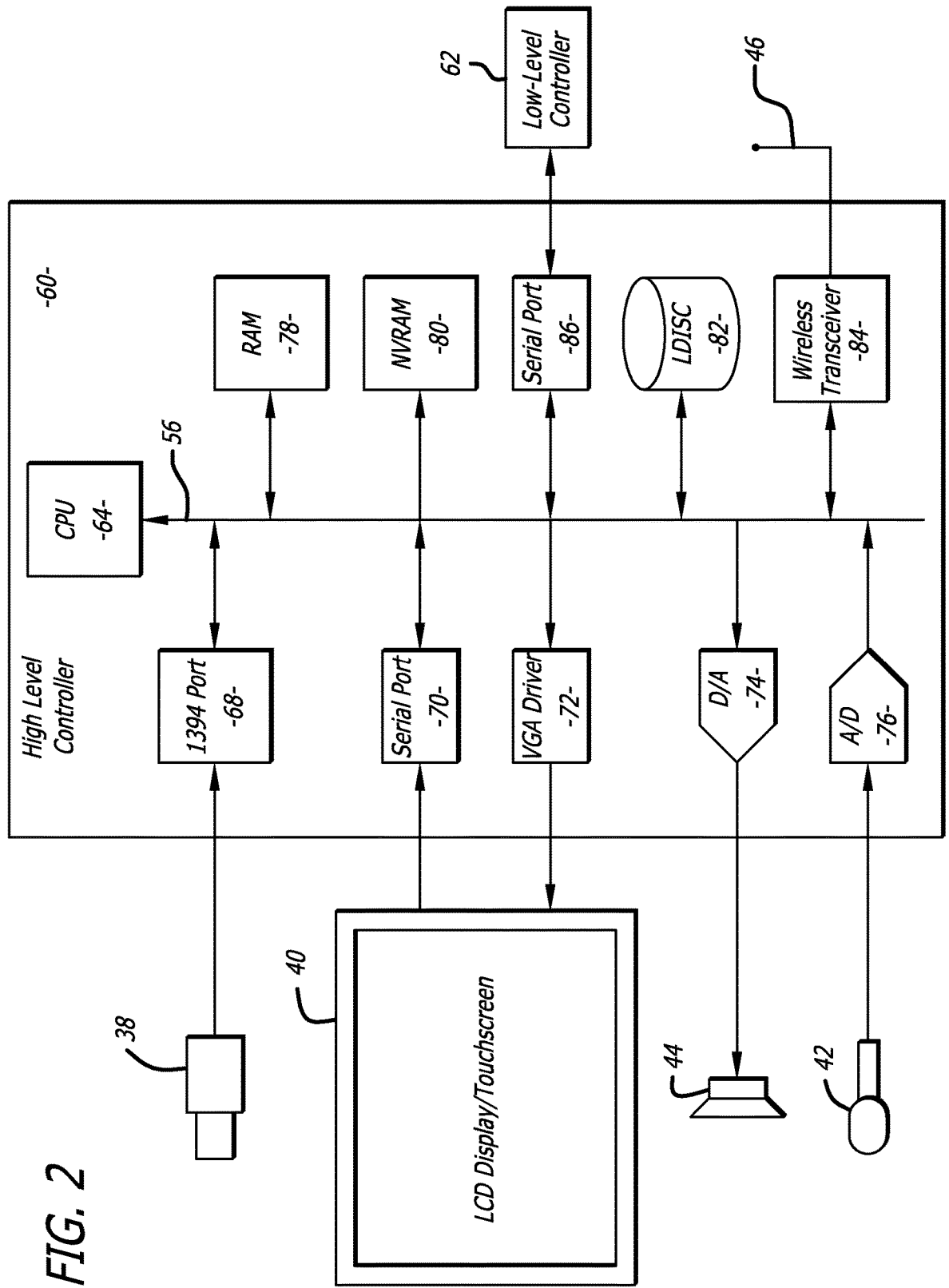
FIG. 2 is a schematic of an electrical system of a robot.

FIG. 2 shows an embodiment of a robot 12. Each robot 12 may include a high level control system 60 and a low level control system 62. The high level control system 60 may include a processor 64 that is connected to a bus 66. The bus is coupled to the camera 38 by an input/output (I/O) port 68, and to the monitor 40 by a serial output port 70 and a VGA driver 72. The monitor 40 may include a touchscreen function that allows the patient to enter input by touching the monitor screen.

The speaker 44 is coupled to the bus 66 by a digital to analog converter 74. The microphone 42 is coupled to the bus 66 by an analog to digital converter 76. The high level controller 60 may also contain random access memory (RAM) device 78, a non-volatile RAM device 80 and a mass storage device 82 that are all coupled to the bus 72. The mass storage device 82 may contain medical files of the patient that can be accessed by the user at the remote control station 16. For example, the mass storage device 82 may contain a picture of the patient. The user, particularly a health care provider, can recall the old picture and make a side by side comparison on the monitor 24 with a present video image of the patient provided by the camera 38. The robot antennae 46 may be coupled to a wireless transceiver 84. By way of example, the transceiver 84 may transmit and receive information in accordance with IEEE 802.11b. The transceiver 84 may also process signals from the medical monitoring device in accordance with IEEE also known as Bluetooth. The robot may have a separate antennae to receive the wireless signals from the medical monitoring device.

The controller 64 may operate with a LINUX OS operating system. The controller 64 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 60 operates to control communication between the robot 12 and the remote control station 16. The low level controller can control movement of the robot 12. The system may be the same or similar to a robotic system provided by the assignee InTouch Technologies, Inc. of Santa Barbara, California under the name RP-7, which is hereby incorporated by reference.

Figure 3:
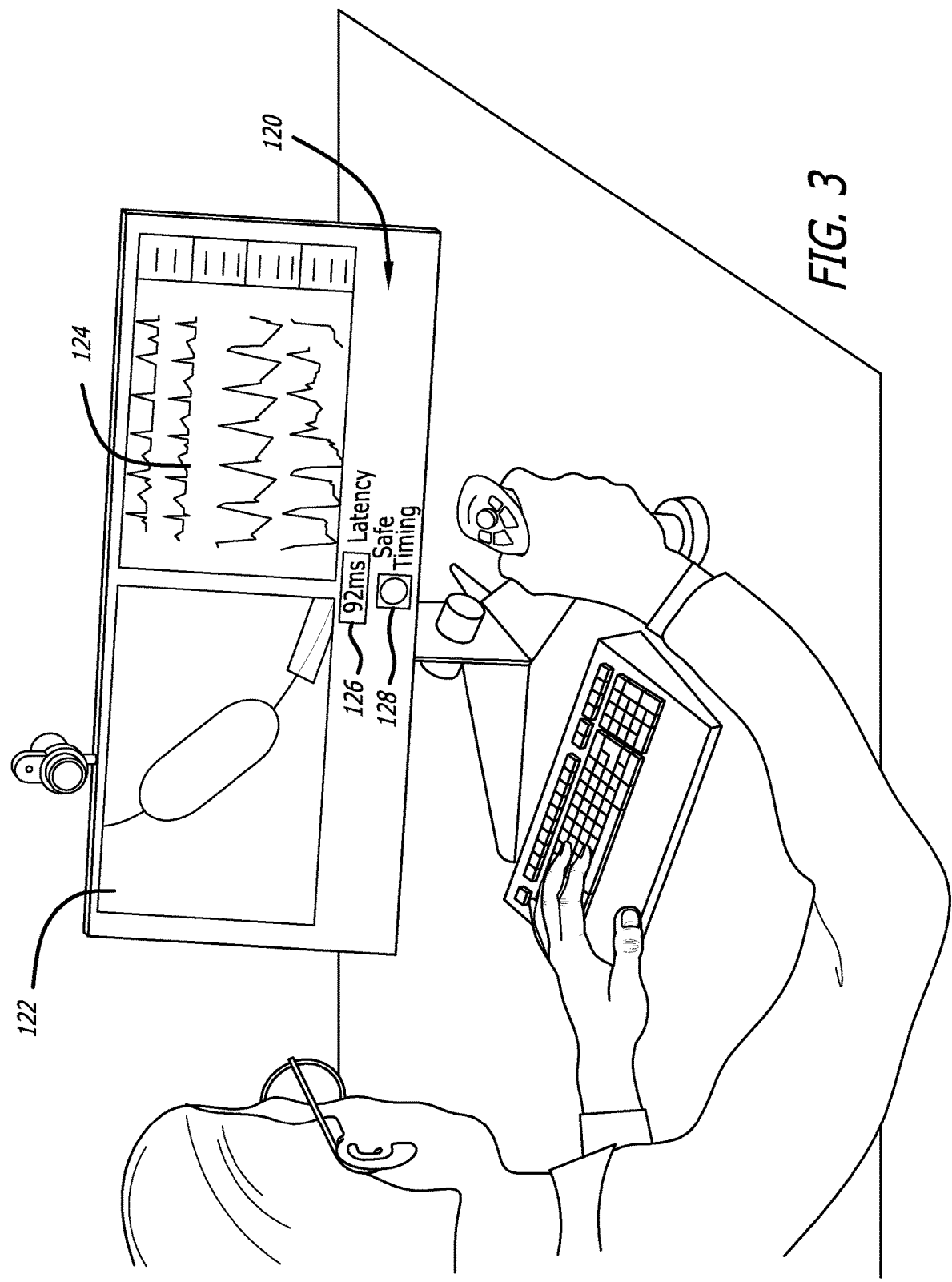
FIG. 3 is a display user interface of a remote station having a first screen field and a second screen field.

FIG. 3 shows a visual display 120 of the remote station. The visual display 120 displays a first screen field 122 and a second screen field 124. The two screen fields may be created by two different monitors. Alternatively, the two screen fields may be displayed by one monitor. The first and second screen fields 122 and 124 may be part of an application program(s) stored and operated by the computer 22 of the remote station 16.

The first screen field 122 can display first information that relates to an action that causes an effect on an object. The second screen field 124 can simultaneously display second information relating to the effect on the object. By way of example, the system can be used for proctoring during a medical procedure. The first screen field 122 may display fluoroscopy imagery showing a stent being inserted through the aorta of a beating heart. The second screen field 124 may display patient hemodynamics such as heart rate. It is critical for the stent to be inserted in a proper position and during certain timing sequences with the beating of the heart. A medical specialist at the remote station can simultaneously view both the position of the stent and the hemodynamic data. This allows the specialist to proctor someone located at the patient location as to the timing of certain stent movement. Proctoring can be accomplished by video and/or audio communication transmitted from the remote station to the robot. Although insertion of a stent is shown and described, the system can be used in any type of procedure such as the deployment of a clot-buster as an example.

The visual display 120 may include a latency indicator 126 that provides the latency between the sending and the receipt of the information displayed in the two synchronized screen fields 122 and 124. For example, FIG. 3 shows a latency of 92 milliseconds between the sending of fluoroscopy imagery and hemodynamic data from the OR, and receipt of the imagery and data at the remote station. Alternatively, the latency value may indicate the round trip latency from OR to remote station and back to the OR, hence representing the time between capture of an image in the OR and receipt of a related proctor instruction in the OR. This latency information may be critical to deployment, as the remote expert must be certain that when stating a command such as 'deploy now', the message is arriving at the proper moment, rather than at an inappropriate time later. The visual display 120 may also include an indicator 128 that provides an indication of when the latency exceeds a threshold. FIG. 4 shows an indication of "Safe Timing" which is displayed when the latency is below the threshold. In one embodiment, a physician may select the type of procedure being proctored from a drop-down menu (not shown), and the threshold value, which represents the maximum safe latency to provide timing-sensitive instructions, will be set from a table of values indexed by procedure type.

The system allows an operator to simultaneously view information that relates to an action that will affect an object and information that relates to the effect on the object. This allows the operator to provide communication to the site of the object, for example a doctor may proctor another doctor at a surgical site.

There are multiple types of procedures that may benefit from this technology. In addition to the transcatheter heart valve deployment described above, the system may be used with a Deep Brain Stimulation (DBS) procedure. The patient's skull is prepared for neurosurgery and is awake, while the surgeon drills through the skull and places scan/stimulation probes in a specific targeted area of the brain. The surgeon simultaneously reads the DBS monitor signs (waveforms and numbers) and then asks the patient to hold up an arm and count down from 100. The patient may struggle with this task. The surgeon may amplify the stimulation to the targeted area of the brain and ask the patient repeat this task until the patient can perform the task with greater ease. In this procedure, the proctoring surgeon must simultaneously see:

(a) the head of the bed where the patient's head is presented, including the local surgeon performing drilling and stimulation;
(b) the DBS monitor relative to what the local surgeon is doing; and possibly
(c) a plan view of the operative field.

In usage, a physician may be in transit when receiving a call requesting proctoring, and may begin the proctoring session while walking to the office, utilizing a mobile device such as an iPad. On the mobile display there may only be space for the flouroscopy imagery, which may be sufficient for proctoring during the initial segment of the procedure only. Upon arrival at the office, the physician may disconnect from the mobile device, which may use 3G and/or 802.11 connectivity, and re-connect from a wide-screen desktop system on an Ethernet connection. The physician may now have high-resolution views of both fluoroscopy and hemodynamics, and may proctor the final deployment. This transition allows for continuity of care across the two devices. Alternatively, the physician may begin using the desktop system while still connected through the mobile device, and the system would effect a seamless automatic disconnect from the mobile device and re-connect to the desktop system.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A proctoring system, comprising:
a communication device at a first location, the first location including a patient, said communication device is coupled to a network and transmits first information and second information, said first information includes real-time fluoroscopy images of said patient received from a fluoroscope coupled to said communication device and said second information includes real-time hemodynamic data of said patient received from a medical monitoring device coupled to said communication device; and,
a remote station at a second location, said remote station is coupled to said communication device and receives said first and second information via the network, said remote station having a visual display that simultaneously displays said first information and said second information, wherein the display of said first information and the display of said second information are synchronized using time stamps inserted into the first and second information before transmission to said remote station, and said remote station includes at least one input device that allows a communication to be transmitted by an operator at said second location to said communication device.

2. The system of claim 1, wherein said communication device includes a monitor and a speaker.

3. The system of claim 2, wherein said communication device includes a mobile platform that is controlled through said remote station.

4. The system of claim 1, wherein said remote station displays a latency that represents a network delay between a local capture of said first information and said second information, and a remote display of said first and second information.

5. The system of claim 1, wherein said remote station displays an indicator that relates to whether a latency exceeds a threshold.

6. The system of claim 1, wherein said at least one input device of said remote station includes a camera and a microphone.

* * * * *